US011236368B2

(12) United States Patent
Steele et al.

(10) Patent No.: US 11,236,368 B2
(45) Date of Patent: Feb. 1, 2022

(54) USE OF BACTERIOCIN-PRODUCING ETHANOLOGENS IN BIOFUEL PRODUCTION

(71) Applicant: Wisconsin Alumni Research Foundation, Madison, WI (US)

(72) Inventors: James L. Steele, Madison, WI (US); Jeffrey Broadbent, Logan, UT (US); Ekkarat Phrommao, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 15/648,872

(22) Filed: Jul. 13, 2017

(65) Prior Publication Data

US 2018/0087073 A1    Mar. 29, 2018

Related U.S. Application Data

(60) Provisional application No. 62/361,783, filed on Jul. 13, 2016.

(51) Int. Cl.
| | |
|---|---|
| *C12N 1/16* | (2006.01) |
| *C12N 1/20* | (2006.01) |
| *C12N 1/38* | (2006.01) |
| *C12P 7/06* | (2006.01) |
| *C12P 7/10* | (2006.01) |

(Continued)

(52) U.S. Cl.
CPC ............ *C12P 7/065* (2013.01); *C07K 14/195* (2013.01); *C12N 1/16* (2013.01); *C12N 1/20* (2013.01); *C12N 1/38* (2013.01); *C12N 9/88* (2013.01); *C12P 7/06* (2013.01); *C12P 7/10* (2013.01); *C12P 7/649* (2013.01); *C12P 21/02* (2013.01); *C12Y 101/01001* (2013.01);
(Continued)

(58) Field of Classification Search
None
See application file for complete search history.

(56) References Cited

U.S. PATENT DOCUMENTS

2011/0262412 A1* 10/2011 Worthington .......... A01N 63/04
424/93.51
2014/0045235 A1   2/2014 Steele et al.
(Continued)

OTHER PUBLICATIONS

Klyachko et al., "Distiller yeasts producing antibacterial peptides", Applied Biochemistry and Microbiology, vol. 51, No. 5, pp. 585-590, Sep. 2015 (Year: 2015).*
(Continued)

*Primary Examiner* — Richard C Ekstrom
(74) *Attorney, Agent, or Firm* — Schwegman Lundberg & Woessner, P.A.

(57) ABSTRACT

An ethanologen for producing biofuel from one or more carbohydrates and reducing lactate and acetate production in a biofuel manufacturing process. The ethanologen is made by introducing into the ethanologen one or more exogenous genes required for production of a bacteriocin. The resulting ethanologen reduces lactate and acetate production by contaminant lactic acid bacteria by expression of the bacteriocin during the biofuel manufacturing process. Certain resulting ethanologens ferment sugars not naturally or not preferentially utilized by *Saccharomyces cerevisiae* during the manufacturing process.

19 Claims, 11 Drawing Sheets

(51) Int. Cl.
    *C12N 9/88*      (2006.01)
    *C07K 14/195*    (2006.01)
    *C12P 7/64*      (2006.01)
    *C12P 21/02*     (2006.01)
(52) U.S. Cl.
    CPC ....... *C12Y 401/01001* (2013.01); *Y02E 50/10* (2013.01); *Y02E 50/30* (2013.01)

(56) References Cited

U.S. PATENT DOCUMENTS

| | | | |
|---|---|---|---|
| 2014/0148379 A1 | 5/2014 | Liu et al. | |
| 2015/0050253 A1* | 2/2015 | Gabant | C12N 1/12 424/93.21 |
| 2015/0320829 A1* | 11/2015 | Liu | C12N 15/52 424/93.6 |

OTHER PUBLICATIONS

Schell et al., Contaminant occurrence, identification and control in a pilot-scale corn fiber to ethanol conversion process, Bioresource Technology, vol. 98, pp. 2942-2948, 2007 (Year: 2007).*
Rana et al., "Genetic modifications and introduction of heterologous pdc genes in Enterococcus faecalis for its use in production of bioethanol", Biotechnology Letters, vol. 34, pp. 1651-1657, 2012 (Year: 2012).*
Nadal I, Rico J, Pérez-Martinez G, Yebra MJ M V: Diacetyl and acetoin production from whey permeate using engineered Lactobacillus casei. J. Ind. Microbiol. Biotechnol. 2009, 36:1233-1237.
Broadbent JR, Neeno-Eckwall EC, Stahl B, Tandee K, Cai H, Morovic W, Horvath P, Heidenreich J, Perna NT, Barrangou R SJ: Analysis of the Lactobacillus casei supragenome and its influence in species evolution and lifestyle adaptation. BMC Genomics 2012, 13:533.
Broadbent JR, Gummalla S, Hughes JE, Johnson ME, Rankin S DM: Overexpression of Lactobacillus casei D-hydroxyisocaproate dehydrogenase in Cheddar cheese. Appl. Environ. Microbiol. 2004, 70:4814-4820.
Broadbent JR, Larsen RL, Deibel V SJ: Physiological and transcriptional response of Lactobacillus casei ATCC 334 to acid stress. J. Bacteriol. 2010, 192:2445-2458.
Budinich M, Diaz-Muñiz I, Cai H, Rankin SA, Broadbent JR SJ: Growth of Lactobacillus paracasei ATCC 334 in a cheese model system: a biochemical approach. J. Dairy Sci. 2011, 94:5263-5277.
Laakso K, Koskenniemi K, Koponen J, Kankainen M, Surakka A, Salusjärvi T, Auvinen P, Savijoki K, Nyman TA, Kalkkinen N, Tynkkynen S VP: Growth phase-associated changes in the proteome and transcriptome of Lactobacillus rhamnosus GG in industrial-type whey medium. Microb. Biotechnol. 2011, 4:746-66.
Van Bokhorst-van de Veen H, Bongers RS, Wels M, Bron PA KM: Transcriptome signatures of class I and III stress response deregulation inLactobacillus plantarum reveal pleiotropic adaptation. Microb. Cell Fact. 2013, 12:112.
Jia K, Zhang Y LY: Systematic engineering of microorganisms to improve alcohol tolerance Eng. Life Sci. 2010, 10:422-429.
Jönsson LJ, Alriksson B NN: Bioconversion of lignocellulose: inhibitors and detoxification. Biotechnol Biofuels 2013, 6:16.
Ling H, Teo W, Chen B, Leong SS CM: Microbial tolerance engineering toward biochemical production: from ignocellulose to products. Curr. Opin. Biotechnol. 2014, 29:99-106.
Nicolaou SA, Gaida SM PE: A comparative view of metabolite and substrate stress and tolerance in microbial bioprocessing: From biofuels and chemicals, to biocatalysis and bioremediation. Metab. Eng 2010, 12:307-331.
Zeng Y, Zhao S, Yang S DS: Lignin plays a negative role in the biochemical process for producing lignocellulosic biofuels. Curr. Opin. Biotechnol. 2014, 27:38-45.
Cold RS, Meagher M, Hutkins R CT: Ethanol tolerance and carbohydrate metabolism in lactobacilli. J. Ind. Microbiol. Biotechnol. 1992, 10:45-54.
Knoshaug EP and MZ: Butanol tolerance in a selection of microorganisms. Appl. Biochem. Biotechnol. 2009, 153:13-20.
Alcántara C, Revilla-Guarinos A ZM: Influence of two-component signal transduction systems of Lactobacillus casei BL23 on tolerance to stress conditions. Appl. Environ. Microbiol. 2011, 77:1516-1519.
Alcátara C ZM: Proteomic and transcriptomic analysis of the response to bile stress of L. casei BL23. Microbiol. 2012, 158:1206-1218.
Morel-Deville F, Fauvel F MP: Two-component signal-transducing systems involved in stress responses and vancomycin susceptibility in Lactobacillus sakei. Microbiol. 1998, 144:2873-2883.
Serrazanetti DI, Guerzoni ME, Corsetti A VR: Metabolic impact and potential exploitation of the stress reactions in lactobacilli. Food Microbiol. 2009, 26:700-711.
Wu C, Huang J, Zhou R: Progress in engineering acid stress resistance of lactic acid bacteria. Appl. Microbiol. Biotechnol. 2014, 98:1055-63.
Tanaka, K., A. Komiyama, K. Sonomoto, A. Ishizaki SJH and PFS: Two different pathways for D-xylose metabolism and the effect of xylose concentration on the yield coefficient of L-lactate in mixed-acid fermentation by the lactic acid bacterium Lactococcus lactis IO-1. Appl. Microbiol. Biotechnol. 2002, 60:160-167.
Posthuma, C. C., R. Bader, R. Engelmann, P.W. Postma WH and PHP: Expression of the xylulose 5-phosphate phosphoketolase gene, xpkA, from Lactobacillus pentosus MD363 is induced by sugars that are fermented via the phosphoketolase pathway and is repressed by glucose mediated by CcpA and the mannose phosphoenolpyr. Appl Environ. Microbiol. 2002, 68:831-837.
Okano K., S. Yoshida, R. Yamada, T. Tanaka, C. Ogino HF and AK: Improved production of homo-D-lactic acid via xylose fermentation by introduction of xylose assimilation genes and redirection of the phosphoketolase pathway to the pentose phosphate pathway in L-lactate dehydrogenase gene-deficient <i>Lactobacillus plant. Appl. Environ. Microbiol. 2009, 75:7858-7861.
Chaillou, S., Yeou-Chemg, Bor, Batt, C. A., Postma, P. W., and Pouwels PH: Molecular cloning and functional experession in Lactobacillus plantarum 80 of xylT, encoding the D-xylose-H+ symporter of Lactobacillus brevis. Appl. Environ. Microbiol. 1998, 64:4720-4728.
Panya M, Lulitanond V, Tangphatsornruang S, Namwat W, Wannasutta R, Suebwongsa N MB: Sequencing and analysis of three plasmids from Lactobacillus casei TISTR1341 and development of plasmid-derived *Escherichia coli*-L. caseishuttle vectors. Appl. Microbial. Biotechnolol. 2012, 93:261-272.
Sudhamani M, Ismaiel E, Geis A, Batish V HK: Characterisation of pSMA23, a 3.5 kbp plasmid of Lactobacillus casei, and application for heterologous expression in Lactobacillus. Plasmid 2008, 59:11-19.
De Ruyter PG, Kuipers OP, Beerthuyzen MM, van Alen-Boerrigter I de VW: Functional analysis of promoters in the nisin gene cluster of Lactococcus lactis . J. Bacteriol. 1996, 178:3434-3439.
Atsumi S, Wu T-Y, Eckl E-M, Hawkins SD, Buelter T, Liao JC: Engineering the isobutanol biosynthetic pathway in *Escherichia coli* by comparison of three aldehyde reductase/alcohol dehydrogenase genes. Appl. Microbiol. Biotechnol. 2010, 85:651-7.

* cited by examiner

Class I: nisin A

Class IIa: pediocin A

Class IIb: brochocin-C

Class IV: carnocyclin A

USE OF BACTERIOCIN-PRODUCING ETHANOLOGENS IN BIOFUEL PRODUCTION

CROSS-REFERENCE TO RELATED APPLICATIONS

This application claims the benefit of U.S. provisional Application No. 62/361,783 filed on Jul. 13, 2016, which is incorporated by reference herein in its entirety.

STATEMENT REGARDING FEDERALLY SPONSORED RESEARCH OR DEVELOPMENT

This invention was made with government support under 2011-67009-30043 awarded by the USDA/NIFA. The government has certain rights in the invention.

FIELD OF THE INVENTION

This disclosure relates generally to biofuel production. More particularly, this disclosure describes microbial ethanologens engineered to produce a bacteriocin, which inhibits contaminant lactic acid bacteria, thereby reducing lactate and acetate production during biofuel production.

BACKGROUND OF THE INVENTION

Microbial production of biofuels from carbohydrates (i.e., corn starch, cane sugar and lignocellulosic substrates) is a component of the United States' plan to reduce its dependency on fossil fuels. The microorganisms typically considered for the production of biofuels include *Saccharomyces cerevisiae*, *Zymomonas mobilis*, *Escherichia coli*, and *Clostridium* sp. However, all of these microorganisms suffer from one or more of the following deficiencies: relatively low tolerance to the environmental stresses likely to be encountered in fermentation (e.g., high levels of alcohols, acids, and/or osmolarity), complex physiology, poor availability of genetic tools, and limited ability to secrete enzymes.

Bacterial contaminants are a chronic problem in biofuel plants which result in significant financial losses to the biofuel industry. The most common bacterial contaminants in ethanol plants are lactic acid bacteria (LAB). These organisms compete with yeast for nutrients, deplete carbohydrates that otherwise would have been converted into biofuel and produce compounds inhibitory to the yeast (i.e., lactate and acetate). It is estimated that the financial loss related to the lactate/acetate problem is approximately $500,000 to $800,000 USD for 50 million gallons of ethanol per year per plant.

At the present time, the majority of the biofuels industry controls these bacterial contaminant issues through the use of antibiotics. However, the use of antibiotics is likely to decline significantly due to concerns related to antibiotics used in biofuel plants entering the human food chain through dried distiller grains with soluble (DDGS), a by-product of the bioethanol industry which contributes 20% of the revenue to an ethanol plant. Major food companies have recognized this concern and publically-stated their intent to no longer source meat from animals that had been raised using DDGS containing antibiotics. A better approach to biofuel production might be to develop a LAB strain capable of outcompeting wild type LAB for nutrients while producing biofuel instead of the deleterious lactate and acetate.

BRIEF SUMMARY OF THE INVENTION

The present invention is a genetically-engineered ethanologen capable of producing one or more bacteriocins, which are antimicrobial peptides produced by one type of bacteria to kill other bacteria, and, preferably, capable of fermenting sugars not naturally or not preferentially utilized by *Saccharomyces cerevisiae*.

This improved ethanologen provides a means of enhancing ethanol production efficiency by reducing inefficiencies caused by bacterial contamination in biofuel plants without the use of antibiotics, and by increasing the total sugars that are converted to ethanol.

Accordingly, in a first aspect, the present invention provides an ethanologen for inhibiting contaminant lactic acid bacteria present in a biofuel manufacturing process. Such an ethanologen includes an ethanologen containing one or more exogenous genes required for production of a bacteriocin, whereby production of the bacteriocin by the ethanologen inhibits contaminant lactic acid bacteria present in the biofuel manufacturing process.

In certain embodiments, inhibition of the contaminant lactic acid bacteria results in reduced lactate and acetate levels in the biofuel manufacturing process.

In certain embodiments, the ethanologen is capable of fermenting sugars not naturally or not preferentially utilized by a main fermenting microbe present in the biofuel manufacturing process, such as *Saccharomyces cerevisiae*.

In certain embodiments, the ethanologen is a native biofuel-producing organism such as a *Sacchoromyces* sp. or *Zymononas* sp. In other embodiments, the ethanologen is an organism engineered to produce a biofuel such as a lactic acid bacterium (i.e., *Lactobacillus* sp., *Lactococcus* sp., *Enterococcus*, sp. or *Streptococcus* sp.), *Escherichia* sp., or *Clostridium* sp.

Exemplary biofuels encompassed by the present invention include ethanol and isobutanol.

Ethanologens according to the invention produce a Class I (lantibiotics), Class IIa (pediocins), Class IIb (two-peptide), or Class IIc (cyclic) bacteriocins. Exemplary bacteriocins useful in the invention include nisin, pediocin, brochocin-C, and carnocyclin A, respectively.

In certain embodiments, an ethanologen of the invention is a *Lactobacillus* sp. engineered to produce the bacteriocin, preferably the species is *Lactobacillus casei* or *Lactobacillus plantarum*. In some embodiments, an ethanologen of the invention is a *Lactococcus lactis* engineered to produce the bacteriocin.

In some embodiments, the exogenous genes required for production of the bacteriocin are operably-linked to an inducible promoter.

Ethanologens of the invention are further envisioned, in certain embodiments, to include one or more immunity genes conferring resistance to the ethanologen against the bacteriocin.

In a second aspect, the present invention provides a bacteriocin-producing ethanologen for use in fermenting additional sugars not naturally or not preferentially utilized by *Saccharomyces cerevisiae* yeast. Exemplary ethanologens according to the invention are able to readily ferment pentose sugars or sugar polymers with a degree of polymerization of 2, 3, 4, or more. Exemplary sugars not naturally or not preferentially utilized by *Saccharomyces cerevisiae* yeast include, e.g., xylose, arabinose, trehalose, maltose, isomaltose, cellobiose, cellobiotriose, maltotriose, isomaltotriose, panose, raffinose, stachyose, maltotetraose, and maltodextrin.

In certain embodiments, the bacteriocin-producing ethanologen is an organism engineered to produce a biofuel and bacteriocin lactic acid bacterium (i.e., *Lactobacillus* sp., *Lactococcus* sp., *Enterococcus* sp., or *Streptococcus* sp.), *Escherichia* sp., or *Clostridium* sp.

In certain embodiments, the bacteriocin-producing ethanologen of the invention is a lactic acid bacterium (i.e., *Lactobacillus* sp., *Lactococcus* sp., *Enterococcus* sp., or *Streptococcus* sp.) engineered to co-utilize glucose and carbohydrates not naturally or not preferentially utilized by a primary fermentor microbe (e.g., *Saccharomyces cerevisiae*), preferably the species being *Lactobacillus casei* or *Lactobacillus plantarum*.

In some embodiments, the bacteriocin-producing ethanologen of the invention is a *Lactococcus lactis* engineered to co-utilize glucose and carbohydrates not naturally or not preferentially utilized by *Saccharomyces cerevisiae* yeast.

In some embodiments, the exogenous genes required for sugar utilization are operably-linked to an inducible promoter.

Ethanologens according to the invention are useful in a broad range of biofuel manufacturing process, including those processes in which the carbohydrate is provided in the form of a lignocellulosic feedstock.

In preferred embodiments, the biofuel manufacturing process is an antibiotic-free process.

In certain embodiments, the ethanologens are hop acid and/or antibiotic-resistant, thereby allowing for utilizing these antimicrobial ingredients with the ethanologen In certain embodiments, the inventive ethanologen is made by a method including the steps of: (a) inactivating within a lactic acid bacterium one or more endogenous genes encoding a lactate dehydrogenase or mannitol dehydrogenase; or (b) introducing into a lactic acid bacterium one or more exogenous genes encoding a pyruvate decarboxylase and one or more exogenous genes encoding an alcohol dehydrogenase II; (c) inactivating within a lactic acid bacterium one or more mannitol dehydrogenases; or (d) performing steps (a), (b) and (c) or a combination of any two steps (a), (b), and (c); and (e) introducing into the lactic acid bacterium the one or more exogenous genes required for production of the bacteriocin; whereby the resulting engineered bacterium produces significantly more ethanol than a wild-type lactic acid bacterium in an ethanol manufacturing process and reduces lactate and acetate production in the process by secretion of the bacteriocin, which inhibits contaminant lactic acid bacteria. The method alternatively or in addition includes one or more steps of: (f) inactivating within a lactic acid bacterium genes encoding proteins such as catabolite control protein A (ccpA) that are associated with catabolite repression or elements related to catabolite repression; (g) removing DNA sequences such as catabolite responsive elements (cre) that are involved in repressing the expression of genes required for uptake and metabolism of sugars not naturally or not preferentially utilized by *Saccharomyces cerevisiae* yeast; (h) introducing into the lactic acid bacterium the one or more exogenous genes required for uptake and metabolism of sugars not naturally or not preferentially utilized by *Saccharomyces cerevisiae* yeast; and (i) introducing into the lactic acid bacterium one or more genes for hop- and/or antibiotic-resistance.

The above method of making the inventive ethanologen may comprise inactivating within the lactic acid bacterium an endogenous gene encoding D-hydroxyisocaproate dehydrogenase. As well, the resulting lactic acid bacterium may include one or more of the following gene deletions: deletion ($\Delta$) of the primary L-lactate dehydrogenase ($\Delta$L-ldh1); $\Delta$ in one or more paralogs of L-lactate dehydrogenase ($\Delta$L-ldh2, $\Delta$L-ldh3, etcetera); $\Delta$ of D-lactate dehydrogenase ($\Delta$D-ldh); and/or $\Delta$ of D-hydroxyisocaproate dehydrogenase ($\Delta$D-hic). The ethanologen may further include gene deletion mutation $\Delta$ mannitol dehydrogenase 1 ($\Delta$mand1) and/or $\Delta$ mannitol dehydrogenase 2 ($\Delta$mand2).

In some embodiments, the exogenous gene encoding a pyruvate decarboxylase comprises the gene of *Zymomonas mobilis* that encodes for pyruvate decarboxylase (Pdc), and the exogenous gene encoding an alcohol dehydrogenase II comprises the gene of *Zymomonas mobilis* that encodes for dehydrogenase II (AdhII). Preferably, the exogenous genes are modified to utilize codon usage preferences of the lactic acid bacterium host strain.

In preferred embodiments, the exogenous genes introduced in the lactic acid bacterium are operably linked to a promoter, such as a lactic acid bacterium such as phosphoglycerate mutase (pgm), as part of an expression vector, such as pPpgm-PET. The promoter is preferably highly expressed in the stationary phase such as, for example, the GroEL promoter, the DnaK promoter, or the UspAC2 promoter.

A particularly useful ethanologen according to the invention is a *Lactobacillus casei* 12A derivative with: (a) a deletion mutation $\Delta$L-ldh1, $\Delta$L-ldh2, and $\Delta$L-ldh3, an exogenous gene encoding a pyruvate decarboxylase, and an exogenous gene encoding an alcohol dehydrogenase II, wherein the exogenous genes are operably linked to a native *L. casei* promoter, and wherein the engineered bacterium produces ethanol at a greater rate than a the wild-type *Lactobacillus casei* 12A bacterium; (b) one or more exogenous genes required for production of a bacteriocin, preferably pediocin, brochocin-C, nisin, or carnocyclin, whereby the etanologen is capable of fermenting sugars not naturally or not preferentially utilized by a main fermenting microbe present in the ethanol manufacturing process. The *Lactobacillus casei* 12A derivative optionally has one or more of: (c) a deletion mutation $\Delta$ccpA; (d) one or more genes required for uptake and utilization of sugars not naturally or not preferentially fermented by *Saccharomyces cerevisiae* yeast; and (e) one or more genes for hop- and/or antibiotic-resistance.

In another aspect, the invention encompasses a method of reducing lactate and acetate production in a biofuel manufacturing process. Such a method includes steps of: (a) culturing an ethanologen according to the invention on a substrate comprising a carbohydrate; (b) reducing lactate and acetate production by contaminant lactic acid bacteria present in the process by the ethanologen's secretion of a bacteriocin; and (c) collecting biofuel produced by the ethanologen. As can be appreciated, the present invention encompasses both the manufacture and use of ethanolgens in reducing lactate and acetate production in a biofuel manufacturing process.

BRIEF DESCRIPTION OF THE DRAWINGS

FIG. 6B. Detail of gene organization in the PET cassette: Ppgm, native promoter from *L. casei* 12A phosphoglycerate mutase; ribosomal binding site (RBS); pdc, pyruvate decarboxylase; adhII, alcohol dehydrogenase; Pin structure, native *L. casei* 12A transcriptional terminator of kdgR transcriptional regulator protein. The cassette was flanked by PstI and BamHI restriction sites for cloning into pTRKH2.

DETAILED DESCRIPTION OF THE INVENTION

I. In General

Figure 1:
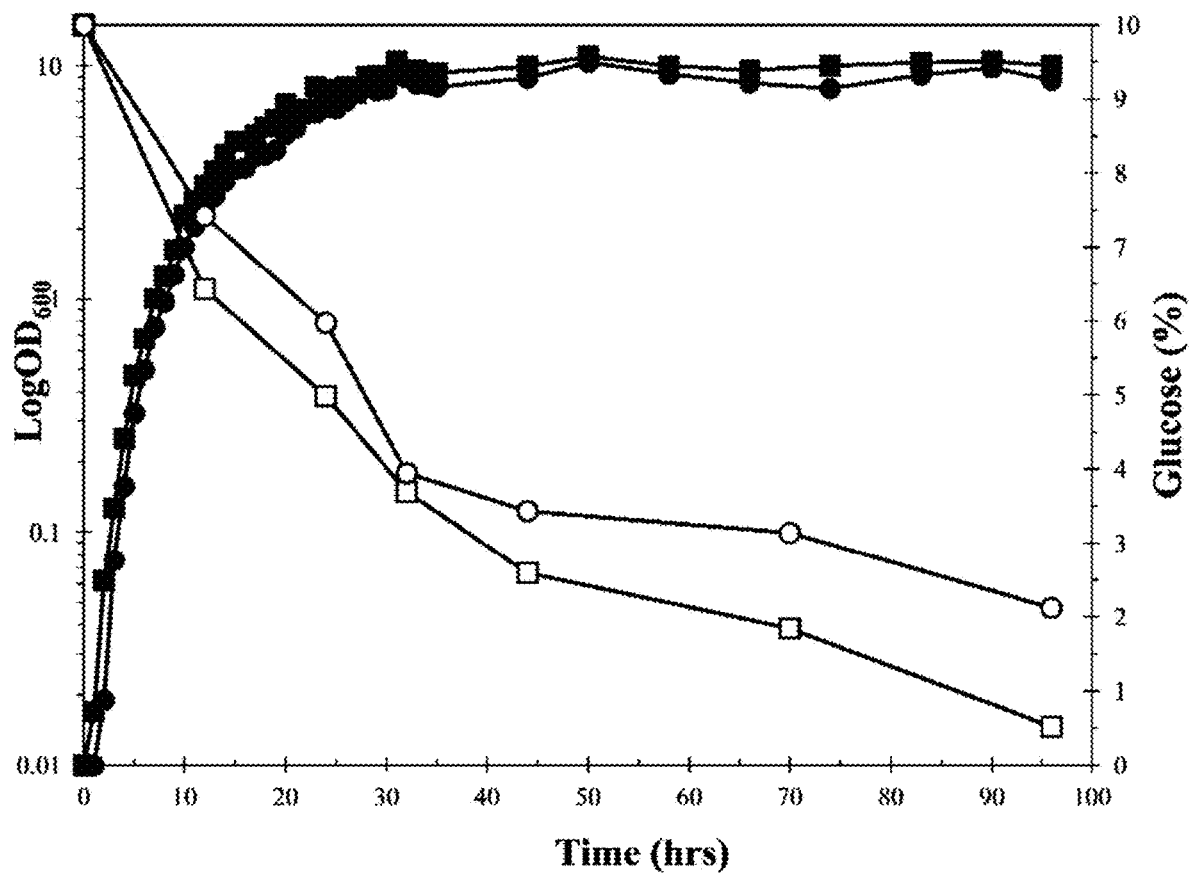
FIG. 1. Growth (■,●) and glucose utilization (□,○) by *Lactobacillus casei* 12A$\Delta$-ldh(pP$_{PGM}$-PET) (squares) and 12A$\Delta$L-Idh1$\Delta$L-Idh2$\Delta$D-hic(pP$_{PGM}$-PET) (circles) at 37° C. in modified chemical defined media (mCDM; Diaz-Muñiz and Steele, 2006) containing 10% glucose (w/v) with pH maintained at 6.0. See Diaz-Muñiz, I. and J. L. Steele, Antonie van Leeuwenhoek 90 (2006): 233-243.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by any later-filed non-provisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising", "including", and "having" can be used interchangeably.

Unless defined otherwise, all technical and scientific terms used herein have the same meanings as commonly understood by one of ordinary skill in the art. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

II. The Invention

The present invention is directed to improving the production efficiency and capacity of bioenergy production from carbohydrates by developing an antibiotic-free process to control bacterial infections in the fermentation and which is also able to convert a greater percentage of the available carbohydrates to biofuel. Bioenergy production via fermentation of carbohydrate is increasing worldwide, and microbial contamination has a strong negative effect on process efficiency and profitability. A variety of microorganisms contaminate bioethanol fermentations, however, lactic acid bacteria (LAB), and particularly lactobacilli, are of primary concern. Losses caused by microbial contamination at individual US bioethanol plants, for example, have been estimated at $14.5 million per year, and there are over 200 bioethanol plants operating in the US. Use of antibiotics, primarily penicillin and virginiamycin, is currently the most common means for control, but this practice has led to the emergence of antibiotic-resistant contaminants, and it may also affect the value of fermentation byproducts such as dried distillers grains with solubles. Thus, research is needed to generate more competitive and innovative solutions for US agriculture-based bioenergy systems.

It is the inventors' hypothesis that representative strains of the most common bacterial contaminants can be metabolically engineered to thwart chronic and acute infections in bioenergy plants, reducing current reliance on antibiotics and increasing bioenergy product yields. Specifically, the inventors hypothesize that ethanologens can be engineered to: i) produce the bioenergy molecule of interest; ii) produce bacteriocins with a broad spectrum of inhibition; iii) be highly resistant to hop acids and antibiotics; and iv) convert to ethanol carbohydrates that are not naturally or not preferentially fermented by the yeast. Used like "starter cultures" for food fermentations, these organisms would be inoculated into the fermentor at the start of each run. The engineered ethanologens will grow to high numbers in the fermentation vessel, killing "wild" bacteria and converting sugars previously used by bacterial contaminants into ethanol rather than lactic or acetic acids. They will also produce ethanol from simple and complex sugars that are not naturally or not preferentially used by yeast. To test the hypothesis, the inventors have used a *Lactobacillus casei* ethanologen they have constructed as a model to demonstrate inhibition—via heterologous expression of different bacteriocins—of bacterial contaminants recovered from bioethanol facilities.

Microbial contamination in bioenergy production. *Saccharomyces cerevisiae* is the biocatalyst of choice in the commercial production of bio-based chemicals such as ethanol and lactate. These fermentations are not conducted under sterile conditions, and selection of a eukaryotic biocatalyst such as *S. cerevisiae* enables the use of antibiotics to control bacterial infections that can impede processing efficiency. For example, it is estimated that approximately 85% of fermentation facilities in the United States producing ethanol from corn starch utilize antibiotics to control bacterial infections. The production of biofuels (both ethanol and isobutanol) from lignocellulosic feedstocks are likely to suffer from even greater difficulties with bacterial infections, as the hurdles to bacterial growth (osmotic pressure and biofuel concentration) are lower in these fermentations. However, there is a growing consensus in the industry that use of antibiotics to control bacterial contamination in commercial biofuel fermentations is a problem, due to the size of the industry and the use of large quantities of a biofuel fermentation by-product, dried distillers grains with solubles (DDGS), as animal feed. Consumer concerns regarding antibiotics in foods has led numerous large food companies (i.e., McDonalds, Walmart, Tyson Foods, Chipotle) to announce they will soon halt the purchase of meat from animals that have consumed or have been treated with antibiotics. An antibiotic-free solution to bacterial contamination of commercial fermentation facilities is urgently needed.

A variety of microorganisms contaminate bioethanol fermentations, however, lactic acid bacteria (LAB), and particularly lactobacilli, are of primary concern. Contamination by lactobacilli results in losses to the bioethanol industry due to both chronic and acute infections. Chronic infections are expected and tolerated, although they significantly reduce productivity, due in large part to the lactobacilli competing with the yeast for carbon and other nutrients. Nonetheless, these losses are substantial with estimates of approximately 0.1 to 1% (w/v) ethanol productivity loss when lactobacilli reach $10^7$ organisms per ml of mash, and higher levels are commonly observed in the industry. Acute infections occur when lactobacilli reach high numbers early in the fermentation, resulting in sufficient lactic acid being produced to inhibit the yeast and cause a "stuck" fermentation. When this occurs, the fermentation facility must be shut down and cleaned. Acute infections have become less common in recent years, but remain a significant financial burden to the ethanol industry. Thus, process improvements that effectively control bacterial contamination without use of antibiotics would substantially improve the production efficiency and capacity of the US agriculture-based bioenergy industry. Such technology would carry the added social benefit of reducing the incidence of antibiotics in human and animal food.

The predominance of LAB contaminants in commercial production of bio-based materials by yeast reflects the fact that yeast and LAB co-inhabit the same environments. Both are commonly found in nutritionally rich environments where their evolutionary strategy involves rapid conversion of carbohydrates into metabolic end products that inhibit competitors. This relationship has been harnessed by humans in the production of a wide array of products including sour dough bread, kefir, sour beers, wine, fish sauce, and soy sauce. Their long-term coexistence likely has resulted in yeasts evolving to be highly resistant to low pH and high levels of organic acids, while LAB have evolved to be among the most alcohol tolerant bacteria known.

This disclosure describes an approach to controlling LAB contamination of industrial yeast bioenergy fermentations that leverages the natural ecology of yeast and LAB. In brief, the inventors use *L. casei* as a model to demonstrate that ethanologens can be engineered to displace contaminating bacteria while simultaneously producing the desired bioenergy molecule from carbon sources that were formerly used by contaminants as well as residual sugars that are not naturally or not preferentially fermented by the biocatalytic yeast. Thus, in addition to controlling LAB contamination, the inventors' approach enhances the production efficiency of bioenergy from fermentation of agricultural feedstocks.

High level innate resistance to many environmental stressors. Microbial biocatalysts often must be highly resistant to a variety of environmental stressors, including elevated concentrations of desired end products. Resistance to inhibitors in lignocellulosic substrates and biofuel products, for example, is one of the most challenging obstacles in the development of an efficient biocatalyst for alcohol production by fermentation [37-41]. The robust nature of *L. casei* and other lactobacilli is evidenced by the ability of these species to grow in high acid, high salt, cold and warm environments with or without oxygen [42]. Moreover, lactobacilli are among the most innately alcohol tolerant (ethanol and isobutanol) microorganisms characterized to date, including *S. cerevisiae, Escherichia coli* and *Clostridium* sp. [37] [40, 43, 44]. This attribute is illustrated by the fact that a *L. casei* 12A-derived ethanologen 12AE1, shows superior growth in modified synthetic corn stover (mSynH) containing 3% ethanol as compared to *Zymomonas mobilis* ATCC 31821 and an *E. coli* ethanologen, GLBRC E1 (Vinay-Lara et al. 2016). Additionally, *L. casei* 12AE1 shows higher innate resistance to osmotic, acetic acid, and lignotoxin stressors in mSynH than *Z. mobilis* ATCC 31821 or *E. coli* GLBRC E1. Furthermore, lactobacilli possess inducible general and specific mechanisms for environmental stress adaptation that can be manipulated to further increase resistance to adverse conditions [17, 20, 26, 45-54]. Collectively, existing knowledge of molecular mechanisms for innate and inducible stress tolerance provides a solid foundation for strain engineering strategies to maximize the fitness of *Lactobacillus*-based platforms.

Ability to utilize lignocellulosic-derived carbohydrates. An intrinsic ability to utilize particular substrates is an important consideration in the selection of a biocatalyst. Co-fermentation of cellobiose and xylose, for example, is particularly important to biofuels fermentation because it supports simultaneous saccharification and fermentation of lignocellulosic feedstocks [55]. *L. casei* and *L. plantarum* possess genes for utilization of many different sugars, including xylose, cellobiose, and other sugars present in lignocellulosic feedstocks [11,56]. The inventors have engineered *L. casei* 12A to co-ferment xylose and glucose. These results illustrate how the rich diversity of carbohydrate utilization genes in lactobacilli can be leveraged to engineer strains suited to a particular biocatalytic process.

Ability to produce and secrete heterologous enzymes. Some bio-manufacturing processes require enzyme pretreatments that add considerable cost to the method. Conversion of lignocellulose into fermentable substrate for biofuels manufacture, for example, is an enzyme intensive process, and lactobacilli such as *L. casei* and *L. plantarum* naturally produces enzymes such as f-glucosidases that could reduce the need for added enzymes. These enzymes are not normally secreted, but lactobacilli have an established record as a host for export of native and heterologous proteins [57-65]. All *Lactobacillus* genomes have been found to carry single copies of SecA, SecE, SecY, YajC and SecG, as well as two copies of YidC [66]. Mathiesen et al. [62] have identified signal sequences for efficient secretion of heterologous proteins by *L. plantarum*, which should function in other *Lactobacillus* species [66]. Additionally, lactobacilli possess several different binding mechanisms for surface associated proteins, including N- or C-terminally anchored proteins, lipoproteins, and LPxTG-anchored proteins [66], which can be exploited for surface localization of heterologous proteins [67-69]. This knowledge provides the foundation needed to engineer *Lactobacillus*-based biocatalysts able to accommodate simultaneous saccharification and bioproducts manufacture.

Bacteriocins. "Bacteriocins," are, as used herein, defined as ribosomally synthesised, proteinaceous substances that inhibit the growth of other bacteria, typically closely related species. These antimicrobial peptides are produced by many bacterial species, including LAB. The bacteriocins produced by LAB have been studied in great depth due to their potential for controlling spoilage and pathogenic microorganisms in foods. These molecules can be divided into two major classes, based on their structural and physical properties. Class I bacteriocins are termed lantibiotics, and include small (<5 kDa), heat-stable peptides that are post-translationally modified to incorporate unusual amino acids such as lanthionine and/or methyllanthionine. Class II bacteriocins are also small (<10 kDa), heat-stable peptides, but these molecules may or may not undergo post-translational modification. Class II bacteriocins are further separated into Class IIa (pediocins and pediocin-like peptides), Class IIb (two-peptide), or Class IIc (cyclic) bacteriocins. Both Class I and Class II bacteriocins include peptides that are active as single peptides as well as two-peptide systems where one or both of the molecules is inactive in single form. Subclasses of Class I and II bacteriocins have also been established based on differences in structure or activity.

Like conventional antibiotics, bacteriocins may exhert bacteriostatic or bactericidal effects on susceptible cells. Conventional antibiotics can be grouped into five major categories according to their target, and bacteriocins from LAB act against at least two of these pathways: disruption of the cell wall synthesis and disruption of the cytoplasmic membrane. The well-characterized Class I lantibiotic nisin, for example, uses lipid II as a docking molecule, and also interacts with the lipid intermediates III and IV. Binding inhibits peptidoglycan synthesis, and triggers subsequent formation of membrane pores that rapidly kill target bacteria. Other lantibiotics (termed "type B") also disrupt cell wall synthesis by binding lipid II but do not form pores.

In contrast, several Class II bacteriocins target membrane components of the mannose-phosphotransferase (man-PTS) system, which somehow triggers permeabilization of the cell membrane and rapid dissipation of the membrane potential. The variations that are observed in host specificity among Class II bacteriocins are proposed to be due to the fact that individual bacteriocins recognize a limited number of the man-PTSs found in different strains or species of bacteria. Finally, some Class II bacteriocins that inhibit cells by disrupting the cytoplasmic membrane do not always target lipid II or the man-PTS. For example, the respective targets for two-peptide bacteriocins plantaricin JK and lactococcin G are an APC superfamily transporter and an enzyme involved in peptidoglycan synthesis, undecaprenyl pyrophosphate phosphatase. Other Class II bacteriocins, including lacticin Q, enterocin AS-48, and carnocyclin A, appear to interact directly with the lipid bilayer.

Spectrum of inhibition. Both within and across different classes, bacteriocins may display narrow or broad range of target species. The inventors' analysis of the microbiological profile in commercial ethanol plants reveal a diversity of LAB species may be present, so successful inhibition of this complex community requires the construction of *L. casei* strains able to produce bacteriocins with a broad spectrum of activity. Nisin, a lantibiotic produced by some strains of *Lactococcus lactis*, and Class II bacteriocins such as pediocin and brochocin C, which are made by strains of pediococci, lactobacilli, and *Brochothrix campestris*, each display broad inhibitory activity against a variety of LAB and other Gram-positive bacteria and have been studied for their efficacy in controlling spoilage microbes in alcoholic fermentations. That examples presented herein demonstrate that addition of nisin to beer fermentation inhibited spoilage bacteria but not brewing yeasts, and a pediocin-producing *Lactobacillus* sp. also inhibited beer spoilage bacteria. The inventors have successfully expressed synthetic gene clusters for pediocin A and brochocin C in an *L. casei* ethanologen, and confirmed the recombinant strain is able to inhibit many of the spoilage bacteria we have collected from commercial ethanol facilities. The present invention encompasses other bacteriocins that: i) show a broad spectrum of activity against Gram-positive bacteria; and/or ii) display different modes of action. The candidates described in the examples section include the lantibiotic nisin, as well as carnocyclin A, a Class IIc cyclic bacteriocin produced by *Carnobacterium maltaromaticum*.

As an exemplary embodiment, the inventors have developed a bioengineered biofuel-producing strain of *Lactobacillus casei*. The following characteristics illustrate why *L. casei* and other lactobacilli are an ideal biofuels fermentation organism: ability to use lignocellulosic-derived mono- and di-saccharides; resistance to environmental stresses likely to be encountered in industrial biofuels fermentations, including high levels of biofuels, acids, and/or osmolarity;

relatively simple fermentative metabolism with almost complete separation of cellular processes for biosynthesis and energy metabolism; possibility to direct metabolic flux of both pentoses and hexoses to pyruvate (allowing for construction of derivatives producing second generation biofuels (i.e., isobutanol); the availability of established platforms for introducing and expressing foreign DNA; availability of a deep portfolio of molecular-genetic data related to their ecological adaptation, genomics, transcriptomics, lipidomics, and metabolomics; the ability to secrete and display proteins, hence potential for use in consolidated bioprocessing; and designation as a GRAS (Generally Regarded As Safe) species.

*L. casei* 12A, a strain isolated from corn silage on the University of Wisconsin-Madison campus, was selected as the biofuels-producing parental strain, due to its alcohol resistance, carbohydrate utilization profile, and amenability to genetic manipulation.

A multi-pronged approach has been employed to redirect metabolic flux in *L. casei* 12A to ethanol. The first approach was to inactivate genes that encode enzymes which compete with the 12A pathway to ethanol. The second approach utilized the introduction of synthetic genes modeled from *Zymomonas mobilis* that encode pyruvate decarboxylase (Pdc) and alcohol dehydrogenase II (Adh2) activities (PET cassette). These synthetic genes were designed utilizing the *L. casei* codon usage for highly expressed genes with a constitutive *L. casei* promoter (phosphoglycerate mutase), synthesized, ligated with digested pTRKH2 to form pP$_{PGM}$-PET), and introduced into 12A derivatives by electroporation. This two pronged approach has resulted in an *L. casei* 12A derivative that produces ethanol as more than 80% of its metabolic end products.

The constructed derivative of *L. casei* 12A described in para. [0061] produces ethanol as more than 80% of its final metabolic end products from glucose. This has been increased to greater than 90% by the inactivation of the two mannitol dehydrogenase genes and the introduction of a second copy of the PET cassette under the control of the UspAC2 promoter. This is by far the greatest conversion that has been reported with a lactobacilli, and will allow us to exploit the advantages of the use of lactobacilli as biocatalysts for the production of biofuels. These advantages are further delineated below.

The present invention further combines converting *Lactobacillus casei* 12A to an ethanologen with the ability to express bacteriocins in lactic acid bacteria (LAB), including *Lb. casei* 12A. The bacteriocins produced by this approach allow the ethanologens to inhibit contaminating lactic acid bacteria (LAB) present in ethanol production processes, thereby reducing the side production of lactate/acetate and enhancing ethanol yield.

The specific features and advantages of the present invention will become apparent after a review of the following experimental examples. However, the invention is not limited to the specific embodiments disclosed herein.

III. EXAMPLES

Example A

This example addresses: (1) what level of carbohydrate *Lactobacillus casei* 12A derivatives are capable of using; and (2) what level of ethanol production takes place at elevated glucose concentrations.

In the first experiment, 48 small volume (2 ml) fermentations were conducted in GC vials containing our *L. casei* chemically defined media to examine glucose utilization and end product formation. In parallel, these fermentations were conducted in a 96 well plate reader to monitor growth. The experimental matrix was: 3 levels of glucose (2.5, 5.0, and 10% w/v), with and without the osmoprotectants present in ACSH (0.7 mM betaine, 0.7 mM choline chloride, and 0.2 mMDL-carnitine), with and without 2.5 μg/ml erythromycin (Ery) to select for the plasmid encoded PET cassette, and four different strains. The strains utilized were: (1) an *L. casei* 12A derivative (12AΔL-ldh1) lacking L-lactate dehydrogenase 1 (L-ldh1), the primary fermentative lactate dehydrogenase, with pTRKH2 (empty vector control); (2) 12AΔL-ldh1 containing pPPGMPET, pTRKH2 with an insert containing the *L. casei* codon optimized *Zymomonas mobilis* genes encoding pyruvate decarboxylase (Pdc) and alcohol dehydrogenase II (Adh2) activities under the control of the *L. casei* phosphoglycerate mutase (pgm) promoter, (3) an *L. casei* 12 A derivative (12AΔL-ldh1ΔL-ldh2ΔD-hic) lacking L-ldh1, L-ldh2, and D-hydroxyisocaproate dehydrogenase (D-Hic) containing pTRKH2; and (4) 12AΔL-ldh1ΔL-ldh2ΔD-hic containing pPPGM-PET. These fermentations were conducted at 37° C. for 96 h and the media had an initial pH of 6.0. Three of the strains (12AΔL-ldh1 (pTRKH2), 12AΔL-ldh(pP$_{PGM}$-PET) and 12AΔL-ldh1ΔLldh2ΔD-hic (pP$_{PGM}$-PET) reached an OD600 of greater than 1.0 within 24 h and grew at indistinguishable rates regardless of the glucose concentration, the presence or absence of either osmoprotectants, or Ery. The other strain, 12AΔL-ldh1ΔL-ldh2ΔD-hic (pTRKH2) grew poorly, never reaching an OD600 of greater than 0.05, even after 96 h, regardless of media composition; this corresponds with previous experiments and was expected, as this strain lacks an efficient mechanism to regenerate NAD+ from pyruvate.

The addition of osmoprotectants did not have a significant effect on growth of any of the strains under the conditions examined; however, the presence of the osmoprotectants did result in a reduction in lysis of strains producing ethanol in the presence of 2.5% glucose. No lysis was observed by the ethanol producing strains at the higher glucose concentrations, suggesting that the higher osmolarities induced genes that provide enhanced ethanol tolerance. The most significant finding from the growth experiments is that growth of *L. casei* 12A derivatives is not affected by the glucose (osmolarity) concentrations up to 10%, rather, these conditions seem to enhance cell viability in stationary phase of 12A derivatives producing ethanol.

Metabolic end product accumulation in the small volume fermentations were determined by GLBRC Enabling Technologies (HPLC-RID), and the results for *L. casei* 12AΔL-ldh (pP$_{PGM}$PET) and 12AΔL-ldh1ΔL-ldh2ΔD-hic (pP$_{PGM}$-PET) are presented in Table 1. All of the glucose was consumed in fermentations containing 2.5% (139 mM) and 5.0% (278 mM) glucose. In fermentations containing 10% (566 mM) glucose, glucose utilization ranged from 8.1 to 9.5% (459.1 to 536.4 mM). The ethanol formed in the 2.5% (139 mM) glucose fermentations ranged from 1.3 to 1.4% (219.6 to 247.6 mM), with % theoretical yields ranging from 79 to 89%. The ethanol formed in the 5.0% (278 mM) glucose fermentations ranged from 2.6 to 2.7% (438.0 to 466.0 mM), with % theoretical yields ranging from 79 to 84%. The ethanol formed in the 10% (566 mM) glucose fermentations ranged from 3.3 to 3.8% (563 to 651.5 mM), with % theoretical yields ranging from 50 to 58%. In fermentations containing 10% (556 mM) glucose, significant accumulation of mannitol (73.2 to 92.4 mM) was observed, suggesting that pyruvate decarboxylase activity has become limiting. Under all the conditions examined, *L.* casei 12AΔLldh1ΔL-ldh2ΔD-hic (pP$_{PGM}$-PET) produced slightly more ethanol and slightly less lactate than *L. casei* 12AΔl-ldh (pP$_{PGM}$-PET). Possible reasons for incomplete glucose utilization in fermentations containing 10% glucose include changes in the pH of the media and increases in pressure due to conducting the fermentations in closed vials. To overcome these issues, fermentations that allow for pH control and $CO_2$ release have been conducted.

Fermentations with 10% glucose with osmoprotectants and Ery have been conducted in our larger scale (500 ml) fermentation equipment that allows for pH control and $CO_2$ release with *L. casei* 12AΔL-ldh (pP$_{PGM}$-PET) and 12AΔL-ldh1ΔL-ldh2ΔD-hic (pP$_{PGM}$-PET) at 37° C., with pH maintained at 6.0. The growth and glucose utilization (enzymatic determination) results are presented in FIG. 1. Growth of the two strains are indistinguishable under these conditions; however, greater glucose utilization was observed by 12AΔL-ldh (pP$_{PGM}$-PET).

The 19 12A derivatives that were constructed via our two-step gene replacement method are presented in Table 2, clearly demonstrating the successful construction of a variety of 12A mutants.

TABLE 1

Metabolic end products accumulated by *L. casei* 12A ethanologens during growth in a chemically defined medium (initial pH 6.0) containing a different levels of glucose, with and without osmoprotectants at 37° C. for 96 hrs.

| Strain | Osmo-protectant | Glucose (mM) | | | Products (mM) | | | | Final pH | % Ethanol (v/v)* |
|---|---|---|---|---|---|---|---|---|---|---|
| | | Int | Con | Rem | EtOH | Man | Lac | Ace | | |
| 12A ΔL-Ldh1 (pP$_{PGM}$ PET) | − | 142.0 | 142.0 | BQL | 227.9 | BQL | 12.3 | 6.6 | 5.4 | 1.3 |
| 12A ΔL-Ldh1 (pP$_{PGM}$ PET) | − | 277.0 | 277.0 | BQL | 438.0 | 14.1 | 26.6 | 4.9 | 4.7 | 2.6 |
| 12A ΔL-Ldh1 (pP$_{PGM}$ PET) | − | 499.7 | 393.7 | 106.0 | 600.0 | 73.2 | 31.8 | 5.3 | 4.5 | 3.5 |
| 12A ΔL-Ldh1 (pP$_{PGM}$ PET) | + | 137.3 | 137.3 | BQL | 219.6 | BQL | 11.8 | 6.6 | 6.2 | 1.3 |
| 12A ΔL-Ldh1 (pP$_{PGM}$ PET) | + | 278.1 | 278.1 | BQL | 445.4 | 3.3 | 39.1 | 3.2 | 4.7 | 2.6 |
| 12A ΔL-Ldh1 (pP$_{PGM}$ PET) | + | 499.3 | 469.6 | 29.6 | 563.0 | 86.1 | 40.5 | 5.3 | 4.4 | 3.3 |
| 12A ΔL-Ldh1/ ΔL-Ldh2/ΔD-Hic (pP$_{PGM}$ PET) | − | 142.3 | 142.3 | BQL | 247.6 | BQL | 7.7 | 8.7 | 7.4 | 1.4 |
| 12A ΔL-Ldh1/ ΔL-Ldh2/ΔD-Hic (pP$_{PGM}$ PET) | − | 282.6 | 282.6 | BQL | 443.5 | 18.3 | 17.9 | 9.1 | 7.2 | 2.6 |
| 12A ΔL-Ldh1/ ΔL-Ldh2/ΔD-Hic (pP$_{PGM}$ PET) | − | 508.0 | 401.1 | 106.9 | 625.0 | 91.6 | 22.3 | 11.7 | 6.6 | 3.6 |
| 12A ΔL-Ldh1/ ΔL-Ldh2/ΔD-Hic (pP$_{PGM}$ PET) | + | 139.5 | 139.5 | BQL | 233.2 | BQL | 7.6 | 8.0 | 6.1 | 1.4 |
| 12A ΔL-Ldh1/ ΔL-Ldh2/ΔD-Hic (pP$_{PGM}$ PET) | + | 280.9 | 280.9 | BQL | 466.0 | 18.1 | 15.2 | 8.3 | 6.7 | 2.7 |
| 12A ΔL-Ldh1/ ΔL-Ldh2/ΔD-Hic (pP$_{PGM}$ PET) | + | 507.9 | 408.9 | 99.0 | 651.5 | 92.4 | 26.0 | 12.4 | 6.8 | 3.8 |

Abbreviations: BQL = Below Quantitative Level.
Abbr: Int—initial, Con—consumed, Rem—remaining, EtOH—ethanol, Man = Mannitol, Lac—Lactate, Ace—acetate.

TABLE 2

*Lactobacillus casei* 12A derivatives constructed in the past 10 months in the Steele laboratory via gene replacement.

| Single knockouts | Double knockouts | Triple knockouts | Quadruple knockouts |
|---|---|---|---|
| ΔL-ldh1* | ΔL-ldh1/ΔL-ldh2* | ΔL-ldh1/ΔL-ldh2/ΔL-ldh3 | ΔoadA/Δpck/Δpyc/Δfum |
| ΔL-ldh2* | ΔL-ldh1/ΔL-ldh3 | ΔL-ldh1/ΔL-ldh2/ΔL-ldh4 | ΔoadA/Δpck/Δpyc/Δaspal |
| ΔL-ldh3 | ΔL-ldh1/ΔL-ldh4 | ΔL-ldh1/ΔLldh2/ΔD-ldh | |
| ΔL-ldh4 | ΔL-ldh1/ΔD-ldh | ΔL-ldh1/ΔL-ldh2/ΔD-hic* | |
| ΔD-ldh | ΔL-ldh1/ΔD-hic | ΔoadA/Δpck/Δpyc | |
| ΔD-hic | ΔL-ldh1/Δpck | | |
| Δals | ΔoadA/Δpck | | |
| Δald | ΔoadA/Δpyc | | |
| Δa/drc | Δpyc/Δpck | | |
| ΔoadA | | | |
| Δpyc | | | |

TABLE 2-continued

*Lactobacillus casei* 12A derivatives constructed in the past 10 months in the Steele laboratory via gene replacement.

| Single knockouts | Double knockouts | Triple knockouts | Quadruple knockouts |
|---|---|---|---|
| Δpck | | | |
| Δaspal | | | |

Abbreviations: L-ldh-L-lactate dehydrogenase, D-ldh D-lactate dehydrogenase, D-hic-D-hydroxyisocaproate dehydrogenase, als-acetolactate synthase, ald-alpha acetolactate decarboxylase, a/drc-acetoin/diacetyl reductase, oad-oxaloacetate decarboxylase,pyc-pyruvate carboxylase,pck-phosphoenolpyruvate carboxikinase, aspal-aspartate-ammonia lyase, fum-fumarase.
Asterisk-derivatives transformed with pP$_{PGM}$-PET are available.

Example B

This example describes analysis of the data the inventors obtained from the fermentations with 10% glucose with osmoprotectants and Ery that were conducted in our larger scale (500 ml) fermentation equipment with *Lactobacillus casei* 12AΔL-ldh (pP$_{PGM}$-PET) and 12AΔL-ldh1ΔLldh2ΔD-hic (pP$_{PGM}$-PET) at 37° C., with pH maintained at 6.0. The inventors could accommodate three fermentation vessels at a time. Therefore, only the 12AΔL-ldh (pP$_{PGM}$-PET) fermentation was conducted in duplicate.

Figure 2:
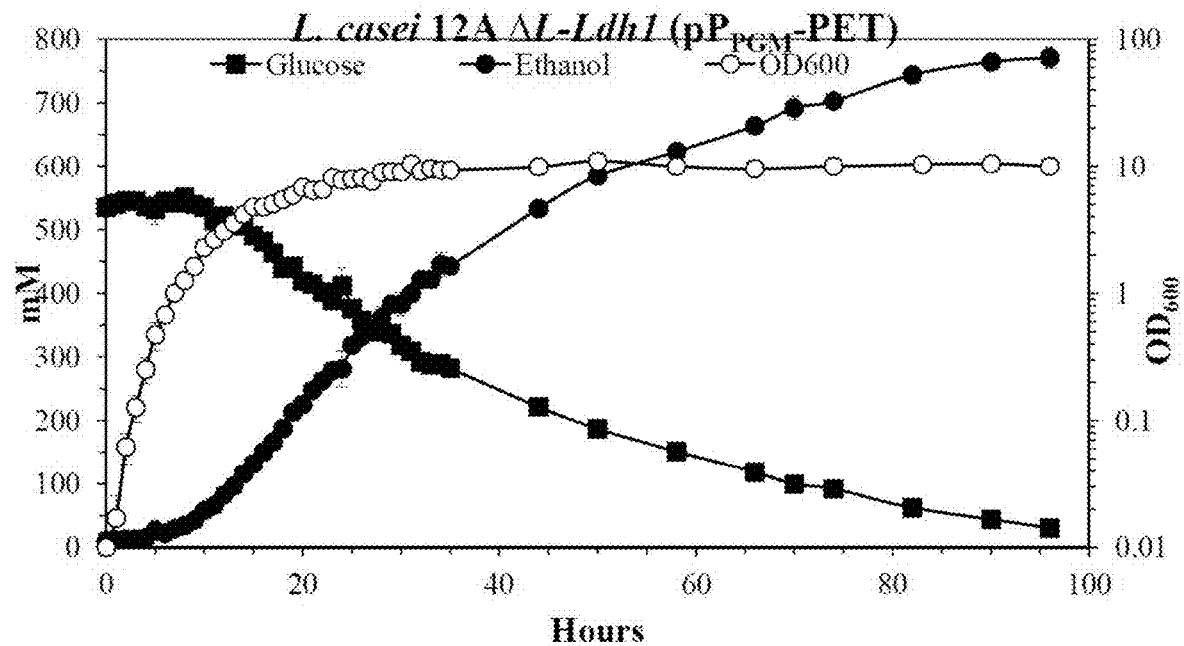
FIG. 2A. Growth, glucose consumption, and ethanol production by *Lactobacillus casei* 12A$\Delta$Lldh1 (pP$_{PGM}$-PET).
FIG. 2B. 12AΔL-ldh1ΔL-ldh2ΔD-hic (pP$_{PGM}$-PET) (2B) at 37° C. in a chemically defined media containing 10% glucose with pH maintained at 6.0.
Figure 2:
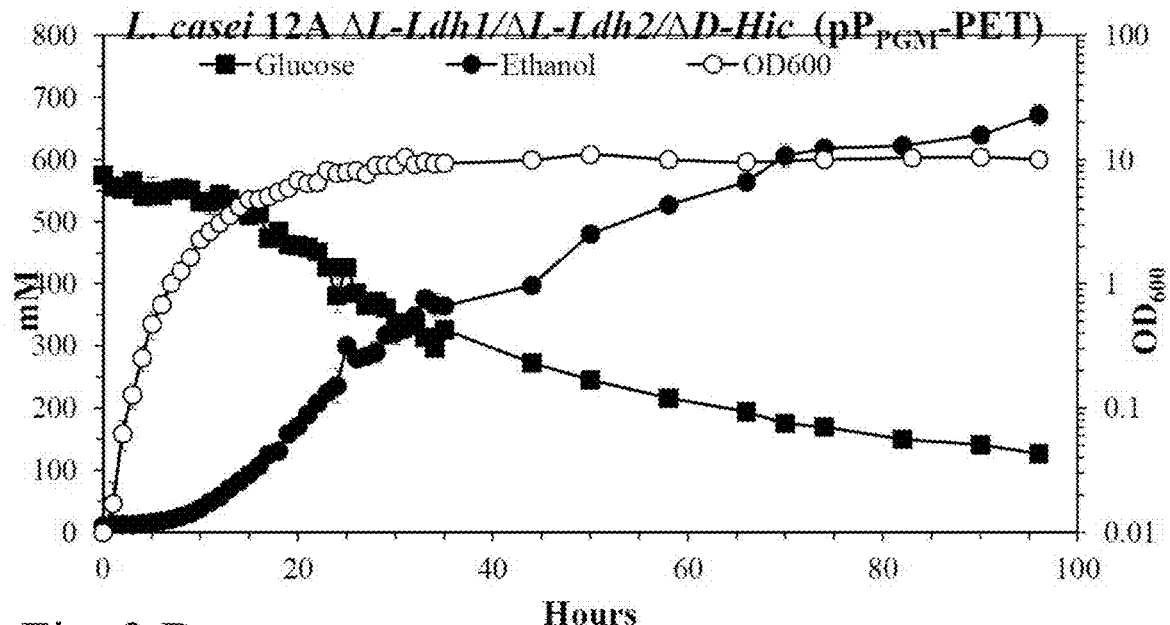

The growth, glucose utilization, and ethanol production shown by these strains are presented in FIG. 2A (*L. casei* 12AΔL-ldh (pP$_{PGM}$-PET)) and 2B (*L. casei* 12AΔL-ldh1ΔLldh2ΔD-hic (pP$_{PGM}$-PET)). The growth of the two strains under these conditions was indistinguishable. However, 12AΔL-ldh (pP$_{PGM}$-PET) utilized a greater quantity of glucose and produced more ethanol than 12AΔL-ldh1ΔL-ldh2ΔD-hic (pP$_{PGM}$-PET). The glucose utilization and ethanol formation obtained with 12AΔL-ldh (pP$_{PGM}$-PET) in the larger fermentation vessels was significantly greater than that obtained in the small volume fermentations described in Example A. The mostly likely reason for this difference is that the larger vessels allow for pH control.

The metabolic end products formed and glucose utilized as a function of time for these fermentations is presented in Tables 3 and 4. 12AΔL-ldh1 (pP$_{PGM}$-PET) will be the focus of this discussion, due to its higher productivity. This 12A derivative utilized 504.5 mM glucose (9.1%) glucose in 96 h and produced 934.7 mM of "pyruvate-derived" metabolic end products, which is 87.4% of the theoretical yield from glucose. Ethanol was produced at a level of 771.3 mM (4.5%), which was 82.5% of the metabolic end-products.

The second most abundant metabolic end product was mannitol, which was present at 110.1 mM after 96 h. Mannitol accumulation began at approximately 21 h, at the same time, ethanol as a percentage of the total metabolic end products began to decrease (% ethanol in total), suggesting that pyruvate decarboxylase activity becomes limiting at that time. This corresponds to the entry of this organism into stationary phase, suggesting that the *L. casei* phosphoglycerate mutase (pgm) promoter used to drive expression of the PET cassette is poorly expressed in stationary phase. Mannitol accumulation was overcome by inactivation of the two mannitol dehydrogenase genes and the introduction of a second copy of the PET cassette under the control of the UspAC2 promoter. This derivative is designated *Lb. casei* E3.

It is difficult to directly compare our results to what is known concerning other biocatalysts, due to differences in media and fermentation equipment utilized. However, the results obtained in these *L. casei* 12AΔL-ldh1 (pP$_{PGM}$-PET) fermentations are most similar to the *Escherichia coli* GLBRCE1 synthetic hydrolysate fermentations reported by Schwalbach et al. (2012, AEM 78:3442) in *E. coli*. GLBRCE1 converted 338 mM glucose into 477 mM ethanol, an ethanol yield of 70.5% of the theoretical maximum. *L. casei* 12AΔL-ldh1 (pP$_{PGM}$-PET) converted 504.5 mM glucose into 771.3 mM ethanol, an ethanol yield of 76.4% of the theoretical maximum.

TABLE 3

Metabolic end products formed and glucose consumption by *Lactobacillus casei* 12A ΔL-Ldh1 (pP$_{PGM}$-PET) at 37° C. in a chemically defined media containing 10% glucose with pH maintained at 6.0.

| Time (hr) | Glucose (mM) Rem | Con | Products (mM) Total | EtOH | Man | Lac | Ace | % yield | % Ethanol in total | % Ethanol (v/v) | Ethanol:Lactate ratio (mM:mM) |
|---|---|---|---|---|---|---|---|---|---|---|---|
| 0 | 534.9 | BQL | 12.5 | 11.1 | 0.0 | 0.1 | 1.2 | 1.2 | 89.2 | 0.1 | 85 |
| 1 | 540.6 | BQL | 22.7 | 12.0 | 0.0 | 5.4 | 5.3 | 2.1 | 52.7 | 0.1 | 2 |
| 2 | 545.2 | BQL | 24.0 | 12.8 | 0.0 | 5.5 | 5.7 | 2.2 | 53.4 | 0.1 | 2 |
| 3 | 544.8 | BQL | 19.2 | 12.8 | 0.0 | 2.5 | 3.8 | 1.8 | 67.0 | 0.1 | 5 |
| 4 | 536.5 | BQL | 21.5 | 15.0 | 0.0 | 2.3 | 4.2 | 2.0 | 70.0 | 0.1 | 7 |
| 5 | 531.4 | BQL | 33.5 | 27.1 | 0.0 | 1.3 | 5.0 | 3.1 | 81.0 | 0.2 | 20 |
| 6 | 544.4 | BQL | 28.2 | 21.7 | 0.0 | 0.9 | 5.6 | 2.6 | 77.0 | 0.1 | 25 |
| 7 | 542.2 | BQL | 36.8 | 29.4 | 0.0 | 1.8 | 5.7 | 3.4 | 79.8 | 0.2 | 17 |
| 8 | 551.2 | BQL | 42.3 | 34.4 | 0.0 | 2.1 | 5.8 | 4.0 | 81.3 | 0.2 | 16 |
| 9 | 539.9 | BQL | 51.2 | 42.8 | 0.0 | 2.7 | 5.8 | 4.8 | 83.5 | 0.2 | 16 |
| 10 | 535.1 | BQL | 67.0 | 58.1 | 0.0 | 3.3 | 5.6 | 6.3 | 86.7 | 0.3 | 18 |
| 11 | 513.9 | 21.0 | 74.9 | 66.1 | 0.0 | 3.6 | 5.2 | 7.0 | 88.2 | 0.4 | 18 |
| 12 | 521.1 | 13.8 | 90.6 | 82.5 | 0.0 | 2.9 | 5.2 | 8.5 | 91.0 | 0.5 | 28 |
| 13 | 512.8 | 22.1 | 105.1 | 96.8 | 0.0 | 3.4 | 4.9 | 9.8 | 92.1 | 0.6 | 29 |
| 14 | 506.3 | 28.7 | 124.5 | 116.1 | 0.0 | 3.9 | 4.4 | 11.6 | 93.3 | 0.7 | 29 |
| 15 | 490.8 | 44.1 | 140.0 | 131.7 | 0.0 | 4.4 | 4.0 | 13.1 | 94.0 | 0.8 | 30 |

TABLE 3-continued

Metabolic end products formed and glucose consumption by *Lactobacillus casei* 12A ΔL-Ldh1 (pP$_{PGM}$-PET) at 37° C. in a chemically defined media containing 10% glucose with pH maintained at 6.0.

| Time (hr) | Glucose (mM) Rem | Glucose (mM) Con | Products (mM) Total | Products (mM) EtOH | Products (mM) Man | Products (mM) Lac | Products (mM) Ace | % yield | % Ethanol in total | % Ethanol (v/v) | Ethanol:Lactate ratio (mM:mM) |
|---|---|---|---|---|---|---|---|---|---|---|---|
| 16 | 481.5 | 53.5 | 158.7 | 150.1 | 0.0 | 4.9 | 3.7 | 14.8 | 94.6 | 0.9 | 31 |
| 17 | 463.4 | 71.5 | 175.4 | 166.6 | 0.0 | 5.4 | 3.4 | 16.4 | 95.0 | 1.0 | 31 |
| 18 | 439.5 | 95.4 | 196.7 | 187.6 | 0.0 | 5.9 | 3.2 | 18.4 | 95.4 | 1.1 | 32 |
| 19 | 442.9 | 92.0 | 223.0 | 213.2 | 0.0 | 6.7 | 3.1 | 20.8 | 95.6 | 1.2 | 32 |
| 20 | 419.4 | 115.5 | 235.4 | 225.5 | 0.0 | 7.0 | 2.8 | 22.0 | 95.8 | 1.3 | 32 |
| 21 | 414.8 | 120.1 | 258.5 | 247.6 | 0.4 | 7.8 | 2.7 | 24.2 | 95.8 | 1.4 | 32 |
| 22 | 402.2 | 132.7 | 275.1 | 263.0 | 1.1 | 8.4 | 2.7 | 25.7 | 95.6 | 1.5 | 31 |
| 23 | 389.1 | 145.8 | 292.6 | 278.7 | 2.1 | 9.2 | 2.5 | 27.3 | 95.3 | 1.6 | 30 |
| 24 | 412.0 | 122.9 | 297.6 | 281.8 | 3.4 | 9.8 | 2.8 | 27.8 | 94.6 | 1.6 | 29 |
| 25 | 375.9 | 159.0 | 336.1 | 318.4 | 4.4 | 10.8 | 2.5 | 31.4 | 94.7 | 1.9 | 29 |
| 26 | 357.3 | 177.6 | 353.2 | 332.4 | 5.7 | 11.8 | 3.3 | 33.0 | 94.1 | 1.9 | 28 |
| 27 | 343.8 | 191.1 | 363.0 | 339.7 | 7.8 | 12.4 | 3.1 | 33.9 | 93.6 | 2.0 | 27 |
| 28 | 339.7 | 195.2 | 387.7 | 362.0 | 9.4 | 13.3 | 2.9 | 36.2 | 93.4 | 2.1 | 27 |
| 29 | 336.6 | 198.3 | 411.0 | 382.9 | 10.5 | 14.3 | 3.2 | 38.4 | 93.2 | 2.2 | 27 |
| 30 | 318.4 | 216.5 | 411.7 | 383.1 | 11.1 | 14.7 | 2.9 | 38.5 | 93.0 | 2.2 | 26 |
| 32 | 292.4 | 242.5 | 451.8 | 421.5 | 12.9 | 15.1 | 2.3 | 42.2 | 93.3 | 2.5 | 28 |
| 34 | 289.7 | 245.2 | 481.8 | 445.1 | 16.3 | 17.4 | 2.9 | 45.0 | 92.4 | 2.6 | 26 |
| 44 | 221.6 | 313.3 | 588.7 | 533.1 | 29.3 | 22.8 | 3.4 | 55.0 | 90.6 | 3.1 | 23 |
| 50 | 187.2 | 347.7 | 656.5 | 584.7 | 41.6 | 25.7 | 4.4 | 61.4 | 89.1 | 3.4 | 23 |
| 58 | 151.4 | 383.5 | 714.0 | 623.4 | 56.3 | 28.5 | 5.8 | 66.7 | 87.3 | 3.6 | 22 |
| 66 | 118.6 | 416.3 | 768.6 | 664.1 | 65.3 | 31.5 | 7.7 | 71.8 | 86.4 | 3.9 | 21 |
| 70 | 99.9 | 435.0 | 813.2 | 691.8 | 78.8 | 33.4 | 9.2 | 76.0 | 85.1 | 4.0 | 21 |
| 74 | 92.2 | 442.7 | 827.3 | 702.8 | 81.3 | 33.8 | 9.4 | 77.3 | 85.0 | 4.1 | 21 |
| 82 | 62.4 | 472.5 | 873.8 | 744.0 | 81.1 | 36.8 | 11.9 | 81.7 | 85.1 | 4.3 | 20 |
| 90 | 44.1 | 490.8 | 913.8 | 764.4 | 97.8 | 38.3 | 13.2 | 85.4 | 83.7 | 4.5 | 20 |
| 96 | 30.4 | 504.5 | 934.7 | 771.3 | 110.1 | 39.2 | 14.1 | 87.4 | 82.5 | 4.5 | 20 |

TABLE 4

Metabolic end products formed and glucose consumption by *Lactobacillus casei* 12A ΔL-Ldh1/ΔL-Ldh2/ΔD-Hic (pP$_{PGM}$-PET) at 37° C. in a chemically defined media containing 10% glucose with pH maintained at 6.0.

| Time (hr) | Glucose (mM) Rem | Glucose (mM) Con | Products (mM) Total | Products (mM) EtOH | Products (mM) Man | Products (mM) Lac | Products (mM) Ace | % yield | % Ethanol in total product | % Ethanol (v/v) | Ethanol:Lactate ratio (mM:mM) |
|---|---|---|---|---|---|---|---|---|---|---|---|
| 0 | 575.3 | BQL | 13.3 | 13.3 | 0.0 | 0.0 | 0.0 | 1.2 | 100.0 | 0.1 | — |
| 1 | 557.1 | 18.3 | 12.9 | 12.9 | 0.0 | 0.0 | 0.0 | 1.1 | 100.0 | 0.1 | — |
| 2 | 553.1 | 22.3 | 12.7 | 12.5 | 0.0 | 0.0 | 0.2 | 1.1 | 98.1 | 0.1 | — |
| 3 | 566.0 | 9.3 | 15.2 | 14.5 | 0.0 | 0.0 | 0.6 | 1.3 | 96.0 | 0.1 | — |
| 4 | 541.8 | 33.6 | 16.7 | 15.2 | 0.0 | 0.0 | 1.5 | 1.5 | 90.9 | 0.1 | — |
| 5 | 548.8 | 26.5 | 21.7 | 18.7 | 0.0 | 0.0 | 3.0 | 1.9 | 86.2 | 0.1 | — |
| 6 | 543.2 | 32.1 | 25.8 | 21.0 | 0.0 | 0.0 | 4.9 | 2.2 | 81.2 | 0.1 | — |
| 7 | 551.2 | 24.1 | 31.6 | 25.5 | 0.0 | 0.0 | 6.1 | 2.7 | 80.6 | 0.1 | — |
| 8 | 554.9 | 20.4 | 36.8 | 30.6 | 0.0 | 0.0 | 6.2 | 3.2 | 83.1 | 0.2 | — |
| 9 | 551.3 | 24.0 | 45.6 | 38.5 | 0.0 | 1.1 | 6.0 | 4.0 | 84.4 | 0.2 | 36 |
| 10 | 532.7 | 42.6 | 55.5 | 48.7 | 0.0 | 0.9 | 5.9 | 4.8 | 87.6 | 0.3 | 53 |
| 11 | 532.3 | 43.0 | 64.5 | 57.7 | 0.0 | 1.1 | 5.8 | 5.6 | 89.4 | 0.3 | 54 |
| 12 | 544.0 | 31.3 | 76.6 | 70.6 | 0.0 | 0.0 | 6.1 | 6.7 | 92.1 | 0.4 | — |
| 13 | 536.6 | 38.7 | 87.7 | 82.1 | 0.0 | 0.0 | 5.6 | 7.6 | 93.6 | 0.5 | — |
| 14 | 519.6 | 55.8 | 101.5 | 93.7 | 0.0 | 2.6 | 5.2 | 8.8 | 92.3 | 0.5 | 36 |
| 15 | 510.2 | 65.1 | 111.9 | 107.0 | 0.0 | 0.0 | 4.9 | 9.7 | 95.7 | 0.6 | — |
| 16 | 513.9 | 61.4 | 134.2 | 125.5 | 0.0 | 3.8 | 4.8 | 11.7 | 93.6 | 0.7 | 33 |
| 17 | 474.2 | 101.1 | 134.7 | 130.7 | 0.0 | 0.0 | 3.9 | 11.7 | 97.1 | 0.8 | — |
| 18 | 485.3 | 90.0 | 167.7 | 158.3 | 0.0 | 5.5 | 3.9 | 14.6 | 94.4 | 0.9 | 29 |
| 19 | 463.7 | 111.6 | 179.9 | 170.4 | 0.0 | 5.9 | 3.5 | 15.6 | 94.8 | 1.0 | 29 |
| 20 | 462.1 | 113.2 | 199.4 | 189.4 | 0.0 | 6.8 | 3.2 | 17.3 | 95.0 | 1.1 | 28 |
| 21 | 459.0 | 116.3 | 218.4 | 207.8 | 0.0 | 7.6 | 3.0 | 19.0 | 95.1 | 1.2 | 27 |
| 22 | 451.9 | 123.5 | 236.9 | 224.9 | 0.7 | 8.6 | 2.8 | 20.6 | 94.9 | 1.3 | 26 |
| 23 | 426.3 | 149.0 | 238.0 | 235.8 | 0.0 | 0.0 | 2.3 | 20.7 | 99.0 | 1.4 | — |
| 24 | 380.6 | 194.7 | 314.8 | 299.9 | 3.5 | 9.4 | 1.9 | 27.4 | 95.3 | 1.8 | 32 |
| 25 | 426.0 | 149.3 | 295.3 | 279.1 | 3.6 | 10.4 | 2.2 | 25.7 | 94.5 | 1.6 | 27 |
| 26 | 384.5 | 190.8 | 297.1 | 283.3 | 2.5 | 9.6 | 1.7 | 25.8 | 95.3 | 1.7 | 29 |
| 27 | 365.0 | 210.3 | 301.5 | 289.6 | 0.5 | 9.6 | 1.8 | 26.2 | 96.1 | 1.7 | 30 |

TABLE 4-continued

Metabolic end products formed and glucose consumption by *Lactobacillus casei*
12A ΔL-Ldh1/ΔL-Ldh2/ΔD-Hic (pP$_{PGM}$-PET) at 37° C. in a
chemically defined media containing 10% glucose with pH maintained at 6.0.

| Time | Glucose (mM) | | Products (mM) | | | | % | % Ethanol in total | % Ethanol | Ethanol:Lactate |
|---|---|---|---|---|---|---|---|---|---|---|
| (hr) | Rem | Con | Total | EtOH | Man | Lac | Ace | yield | product | (v/v) | ratio (mM:mM) |
| 28 | 371.3 | 204.1 | 331.6 | 317.2 | 1.7 | 11.0 | 1.6 | 28.8 | 95.7 | 1.9 | 29 |
| 29 | 360.5 | 214.8 | 339.2 | 320.3 | 5.6 | 10.9 | 2.3 | 29.5 | 94.4 | 1.9 | 29 |
| 30 | 332.9 | 242.4 | 341.2 | 326.4 | 2.9 | 10.9 | 1.0 | 29.7 | 95.7 | 1.9 | 30 |
| 32 | 333.5 | 241.8 | 395.1 | 375.6 | 5.8 | 12.5 | 1.2 | 34.3 | 95.1 | 2.2 | 30 |
| 34 | 296.7 | 278.6 | 381.7 | 363.9 | 5.3 | 12.1 | 0.4 | 33.2 | 95.3 | 2.1 | 30 |
| 44 | 272.5 | 302.8 | 520.6 | 480.5 | 22.4 | 14.4 | 3.2 | 45.2 | 92.3 | 2.8 | 33 |
| 50 | 245.1 | 330.2 | 578.6 | 527.3 | 30.5 | 16.6 | 4.2 | 50.3 | 91.1 | 3.1 | 32 |
| 58 | 216.0 | 359.4 | 627.0 | 564.1 | 39.4 | 17.6 | 5.8 | 54.5 | 90.0 | 3.3 | 32 |
| 66 | 194.1 | 381.3 | 681.0 | 606.2 | 49.2 | 18.3 | 7.2 | 59.2 | 89.0 | 3.5 | 33 |
| 70 | 175.2 | 400.1 | 700.5 | 618.2 | 54.8 | 19.5 | 8.0 | 60.9 | 88.3 | 3.6 | 32 |
| 74 | 169.5 | 405.8 | 706.8 | 622.6 | 56.7 | 19.2 | 8.3 | 61.4 | 88.1 | 3.6 | 32 |
| 82 | 149.8 | 425.5 | 712.2 | 639.6 | 63.1 | 0.0 | 9.5 | 61.9 | 89.8 | 3.7 | — |
| 90 | 141.0 | 434.3 | 752.9 | 672.0 | 70.1 | 0.0 | 10.8 | 65.4 | 89.3 | 3.9 | — |
| 96 | 126.6 | 448.7 | 774.2 | 663.1 | 79.0 | 21.1 | 10.7 | 67.3 | 85.7 | 3.9 | 31 |

Glucose))×100% Ethanol=(mmol/L ethanol×46.068 g/mol)/(1000 mg/g)×(1000 ml/L/100 ml)×(0.789 g/ml).

Example C

Screening Strains of *L. casei* for Biofuels' Relevant Phenotypes and Genes.

Our laboratory has a culture collection which contains approximately 60 strains of *L. casei* isolated from green plant material (i.e., corn silage), cheese, wine, and humans. The eleven strains with genome sequences were screened for the ability to utilize 60 different carbohydrates, including numerous carbohydrates present in lignocellulosic feed stocks. Individual strains were able to grow on between 17 and 26 different substrates. The strains isolated from corn silage (12A and 32G) grew on the greatest number of substrates. Nine gene clusters potentially involved in cellobiose utilization and one gene cluster involved in xylose utilization were identified.

The eleven strains with genomic information were also screened for alcohol tolerance (ethanol, 1-propanol, 1-butanol, and 2-methyl-1-butanol), growth in AFEX-pretreated corn stover hydrolysate (ACSH), and transformation (electroporation) efficiency. *L. casei* 12A exhibited the greatest tolerance to the biofuels examined. For example, when grown in the presence of 10% ethanol, it reached a final cell density 40% of that it attained in the absence of ethanol. Of the 11 strains examined for growth in corn stover hydrolysate, 3 of these strains (ATCC 334, 21-1, and 12A) grew significantly better, reaching a final optical density at 600 nm of approximately 2.0 within 28 h. Five *L. casei* strains were examined for transformation efficiency with pTRKH2 (O'Sullivan and Klaenhammer 1993). *L. casei* 12A exhibited a frequency (approximately 5×10$^5$ transformants per ug of pTRKH2) at least 50-fold higher than that observed with any of the other strains examined. Based upon the results from these analyses, *L. casei* 12A was selected as the biofuel producing parental strain.

Completing the *L. casei* 12A Genome.

For further information regarding the *L. casei* 12A genome, see Broadbent, et al., *BMC Genomics* 2012, 13:533, which is incorporated by reference herein. To enhance the depth of genomic sequence coverage of 12A, genomic DNA was prepared and submitted to the Joint Genome Institute (JGI) for genome sequencing. A draft genome of *L. casei* 12A with approximately 500× coverage assembled into 397 scaffolds was received from JGI. This genome assembly was subsequently merged with the previous 23×454-generated paired end genome assembly in collaboration with personnel from DuPont Inc. (Madison, Wis.), yielding a genome assembly with 19 ordered contigs. We have generated PCR amplicons across all 19 gaps, and have sequenced 10 of these amplicons.

*L. casei* Metabolic Models.

We have developed a genome-scale metabolic model for *L. casei* ATCC334 (the neotype strain) and 12A using the ModelSEED database and the genome annotation from RAST. We have modified the draft *L. casei* 12A model from ModelSEED using the following processes: 1) thermodynamically infeasible cycles were removed, 2) elementally imbalanced metabolic reactions were corrected; and 3) model predictions for amino acid requirements were compared against experimental growth phenotypes determined in a lactobacilli chemically defined medium (CDM) described by Christensen and Steele (J. Bacteriol. 185 (2003): 3297-3306). Inconsistencies were corrected by the addition or deletion of some reactions.

Redirecting Metabolic Flux in *L. casei* 12A to Ethanol.

The development of a method to inactivate genes in *L. casei* was a requirement for the construction of a *L. casei* strain capable of converting lignocellulosic biomass to ethanol. An efficient gene replacement method based on the introduction of pCJK47-based constructs (Kristich et al. 2007) via a 12A optimized electroporation protocol was developed.

A multi-pronged approach was employed to redirect metabolic flux in *L. casei* 12A to ethanol. The first approach is to inactivate genes that encode enzymes which compete with the 12A pathway to ethanol, which has acetyl-CoA as an intermediate. There are a large number of genes that encode enzymes potentially involved in anaerobic pyruvate metabolism in *L. casei*. We have inactivated 9 of these genes: pyruvate-formate lyase (Pfl), the four L-lactate dehydrogenases (L-ldh1, Lldh2, L-ldh3, and L-ldh4), D-lactate dehydrogenase (D-ldh), D-hydroxyisocaproate dehydrogenase (DHic), acetolactate synthase (Als), and oxaloacetate decarboxylase (OadA). Additionally, 5 derivatives lacking two or three of the dehydrogenases have been constructed. Characterization of the end product distribution these mutants is presented in Table 5. The highest level of metabolic redirection to ethanol achieved to date using this approach, is 21%, achieved with the 12A ΔL-ldh1ΔL-ldh2ΔD-hic derivative. This derivative was determine to accumulate mannitol under high carbohydrate loading. Mannitol accumulation was overcome by inactivation of the two mannitol dehydrogenase genes and the introduction of a second copy of the PET cassette under the control of the UspAC2 promoter. This derivative is designated Lb. casei E3.

The second approach utilized to direct metabolic flux in 12A towards ethanol was the introduction of synthetic genes modeled from Zymomonas mobilis that encode pyruvate decarboxylase (Pdc) and alcohol dehydrogenase II (Adh2) activities (PET cassette). These genes were designed utilizing the L. casei codon usage for highly expressed genes with a constitutive L. casei promoter (phosphoglycerate mutase), synthesized by GeneArt, ligated with digested pTRKH2 (pPGM-PET), and introduced into 12A derivatives by electroporation. Characterization of the end product distribution of two of these derivatives has been completed and is presented in Table 5. The highest level of metabolic redirection to ethanol achieved to date using this approach is 85.3%, achieved with the 12A ΔL-ldh1ΔL-ldh2 (pP$_{PGM}$-PET) derivative. It is interesting to note that 12A derivatives with pP$_{PGM}$-PET grow more rapidly than their corresponding strains, suggesting that ethanol is less inhibitory to 12A derivatives than lactate.

These results suggest that the multi-pronged approach is effective for redirecting 12A metabolic flux to ethanol.

Example D. Conversion of a Lactic Acid Bacterium Lactobacillus casei 12A to an Ethanologen Lactobacillus casei 12A was selected as the biofuels parental strain based upon its alcohol tolerance (grows in the presence of >10% ethanol), carbohydrate utilization, and relatively high transformation efficiency. This organism metabolizes hexoses through the Embden-Meyerhof-Parnas pathway and converts pyruvate to lactate via a variety of different enzymes; including four L-lactate dehydrogenases (Ldh), one D-Ldh, and one D-hydroxyisocaproate dehydrogenase.

Essential characteristics of organisms to be utilized for microbial production of ethanol from plant biomass include the ability to secrete enzymes, transport glucose and xylose, metabolize glucose and xylose to ethanol, as well as have sufficient ethanol tolerance to make the fermentation economically viable. It is unlikely an organism capable of meeting all of these criteria will be isolated from nature. Therefore, rational strategies to engineer strains for the industrial production of ethanol from plant biomass are preferred. The following characteristics make L. casei 12A an ideal Gram-positive species for research in this area:

Designation as a GRAS (generally Regarded As Safe) species.

Established platforms for introducing and expressing foreign DNA.

TABLE 5

Growth, substrate consumption, and metabolic end products formed by Lactobacillus casei 12A and derivatives during growth in a chemically defined media at 37° C. for 48 hrs.

| | Growth | | Substrate | | Concentration (mM) | | | | | | EtOH/ | |
| | | | | | | Metabolic End Products | | | | | | |
| | Max | T$_d$ | Utilization$^a$ | | | (% of total)$^b$ | | | | | Yield | Lac |
| Derivative | OD$_{600}$ | (h.) | Glc | Cit | Total | L-lac | D-lac | EtOH | Ace | Man | (%)$^c$ | ratio$^d$ |
|---|---|---|---|---|---|---|---|---|---|---|---|---|
| 12A | 1.05 | 8.1 | 51.5 | 0.6 | 112.2 | 105.4, (94) | 3.3, (3) | 1.4, (1) | 2.1, (2) | BQL | 108 | 0.0 |
| 12A ΔL-ldh1 | 1.28 | 7.0 | 52.6 | 11.5 | 87.0 | 42.3, (49) | 28.2, (32) | 16.5, (19) | BQL | BQL | 68 | 0.2 |
| 12A ΔL-ldh2 | 1.01 | 8.3 | 53.1 | 5.8 | 111.8 | 105.0, (94) | 3.2, (3) | 1.6, (1) | 2.0, (2) | BQL | 95 | 0.0 |
| 12A ΔL-ldh3 | 1.02 | 8.0 | 52.7 | 9.0 | 110.2 | 103.0, (94) | 3.2, (3) | 2.1, (2) | 1.9, (2) | BQL | 90 | 0.0 |
| 12A ΔD-ldh | 1.02 | 7.7 | 51.9 | BQL | 112.4 | 103.5, (92) | 5.4, (5) | 1.1, (1) | 2.4, (2) | BQL | 108 | 0.0 |
| 12A ΔD-hic | 1.26 | 7.9 | 51.5 | BQL | 112.0 | 109.7, (98) | BQL | 0.5, (1) | 1.8, (2) | BQL | 109 | 0.0 |
| 12A ΔL-ldh1/ ΔD-ldh | 1.26 | 7.1 | 52.8 | 15.0 | 86.7 | 32.1, (37) | 42.6, (49) | 12.0, (14) | BQL | BQL | 64 | 0.2 |
| 12A ΔL-ldh1/ ΔD-hic | 1.11 | 9.7 | 51.2 | 13.9 | 79.8 | 64.9, (81) | BQL | 14.9, (19) | BQL | BQL | 61 | 0.2 |
| 12A ΔL-ldh1/ ΔL-ldh2/ΔD-ldh | 0.93 | 9.4 | 52.5 | 10.3 | 71.4 | BQL | 51.5, (72) | 18.6, (26) | BQL | 1.3, (2) | 57 | 0.4 |
| 12A ΔL-ldh/ ΔL-ldh2/ΔD-hic | 0.52 | 31.3 | 21.7 | 12.8 | 36.1 | 0.6, (2) | 0.4, (1) | 7.6, (21) | 7.2, (20) | 20.3, (56) | 52 | 7.6 |
| 12A (pTRKH2) | 1.01 | 13.2 | 52.5 | BQL | 108.9 | 100.4, (92) | 7.6, (7) | BQL | 0.9, (1) | BQL | 104 | 0.0 |
| 12A (pPGM-PET) | 0.95 | 6.79 | 51.3 | 8.2 | 95.1 | 14.8, (16) | 13.2, (14) | 58.1, (61) | 9.0, (10) | BQL | 80 | 2.1 |
| 12A ΔL-ldh1 (pTRKH2) | 1.11 | 11.3 | 52.3 | 2.7 | 87.7 | 41.6, (47) | 34.0, (39) | 12.1, (14) | BQL | BQL | 80 | 0.2 |
| 12A ΔL-ldh1 (pPGM-PET) | 1.03 | 6.8 | 51.0 | 16.3 | 102.1 | 2.7, (3) | 5.0, (5) | 84.5, (83) | 9.8, (10) | BQL | 76 | 10.9 |
| 12A ΔL-ldh1/ ΔL-ldh2 (pPGM-PET) | 1.01 | 7.9 | 50.9 | 16.0 | 100.2 | 0.7, (1) | 5.1, (5) | 85.3, (85) | 9.1, (9) | BQL | 75 | 14.7 |

$^a$Reported by the initial concentration of glucose or citrate subtracted by the fetal concentration of the respective compound at 48 hrs.
$^b$In parenthesis, metabolic end product distribution by % of total.
$^c$Calculated by percentage of total metabolic end products produced/2 × (glucose + citrate) in mmoles.
$^d$Expressed as molar ratio, where lactate is the summation of both the L- and D- forms.
Abbreviations: BQL = below quantifiable level; NA = not applicable; Glu = glucose; Cit = citrate; Lac = lactate; ETOH = ethanol; Ace = acetate; Man = mannitol Relatively simple fermentative metabolism with almost complete separation of cellular processes for biosynthesis and energy metabolism.

Resistance to environmental stress, including high concentrations of acids and biofuels Ability to use lignocellulosic carbohydrates.

Ability to secrete and display proteins, hence potential for use in consolidated bioprocessing.

Multiple strategies were pursued concurrently to redirect *L. casei* 12A fermentation to ethanol. The first strategy involved inactivation of enzymes that consume pyruvate under anaerobic conditions without producing ethanol, including the D-Ldh; four L-Ldhs; D- (D-Hic); acetolactate synthase (Als); and oxaloacetate decarboxylase (Oad). This approach has been used to inactivate L-ldh1, L-ldh2, and D-hic, as well as to construct the L-ldh1/L-ldh2, double mutant. The highest level of ethanol formation was observed with the ΔL-ldh1/ΔL-ldh2 double mutant, which produces ethanol as 14% of its metabolic end products.

Our second strategy for increasing flux to ethanol involved expressing ethanol producing enzymes. A codon optimized "PET" cassette comprised of synthetic *Zymomonas mobilis* genes encoding pyruvate decarboxylase (Pdc) and alcohol dehydrogenase (Adh2) was constructed, and placed under the control of the *L. casei* 12A pgm promoter, pgm ribosomal binding site and kdgR transcriptional terminator. When this construct was introduced into *L. casei* 12A, ethanol made up 61% of metabolic end products formed. When introduced into *L. casei* 12A (ΔL-ldh1), ethanol was the dominant product observed (91% of metabolic end productions). Results from this analysis indicate that the two approaches are complementary and demonstrate that redirecting metabolic flux in *L. casei* from lactate to an alcohol can be readily achieved. The organism described above was determine to accumulate mannitol under high carbohydrate loading. Mannitol accumulation was overcome by inactivation of the two mannitol dehydrogenase genes and the introduction of a second copy of the PET cassette under the control of the UspAC2 promoter. This derivative is designated *Lb. casei* E3.

Figure 3:
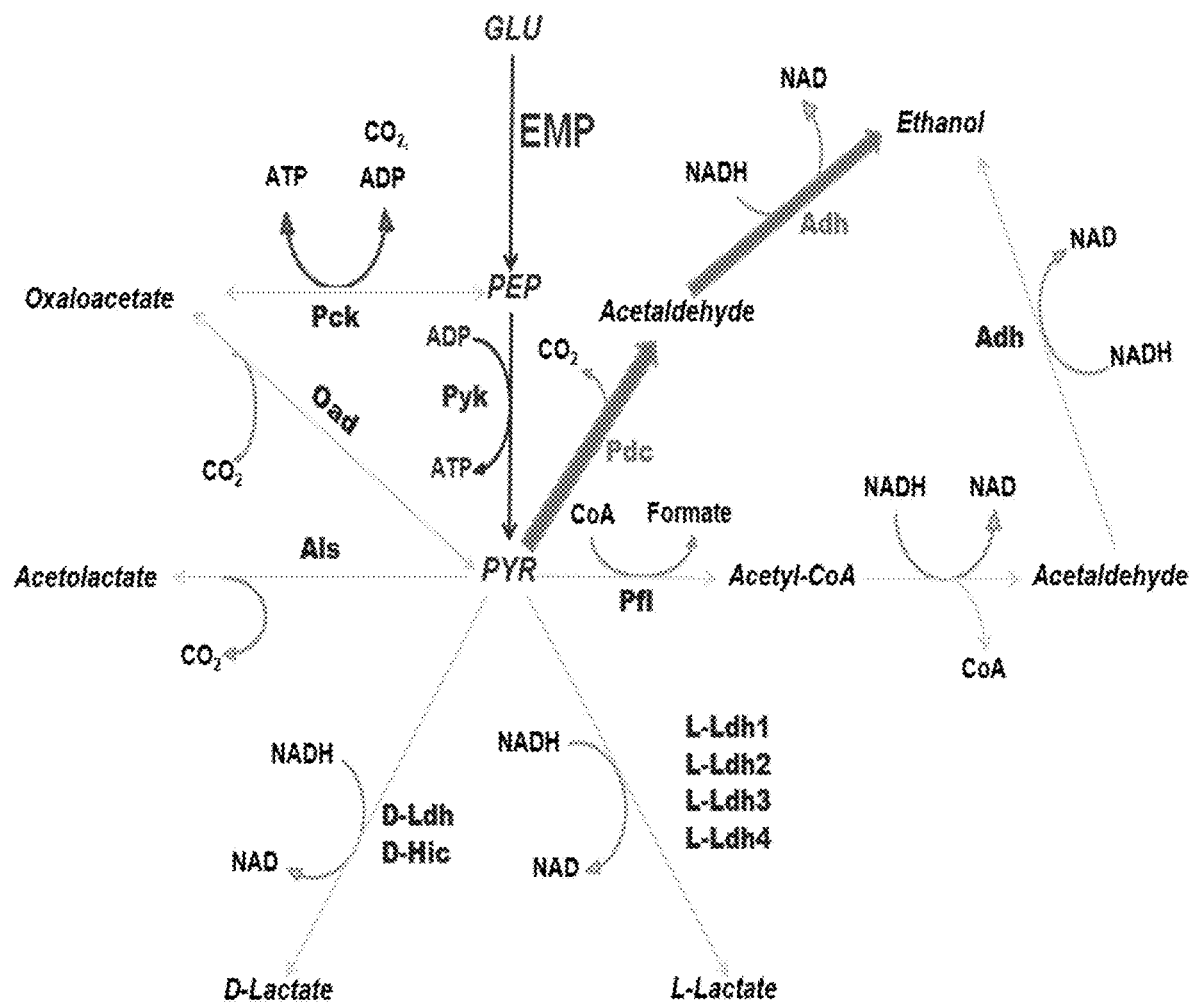
FIG. 3. Metabolism of pyruvate (PYR) in *Lactobacillus casei* 12A and derivatives. The pyruvate related enzymes and pathways present in *L. casei* 12A: L-lactate dehydrogenases (L-Ldh); D-lactate dehydrogenase (D-Ldh); D-Hydroxyisocaproate dehydrogenase (D-Hic); acetolactate synthase (Als); oxaloacetate decarboxylase (Oad); pyruvate kinase (Pyk); phophoenolpyruvate carboxikinase (Pck); pyruvate-formate lyase (Pfl); alcohol dehydrogenase (Adh). The enzymes and pathway from *Zymomonas mobilis* are shown as thick arrows: pyruvate decarboxylase (Pdc); alcohol dehydrogenase (Adh). Abbreviations: EMP, Embden-Meyerof-Parnas pathway; Glu, glucose; PEP, phosphoenolpyruvate.
Figure 4:
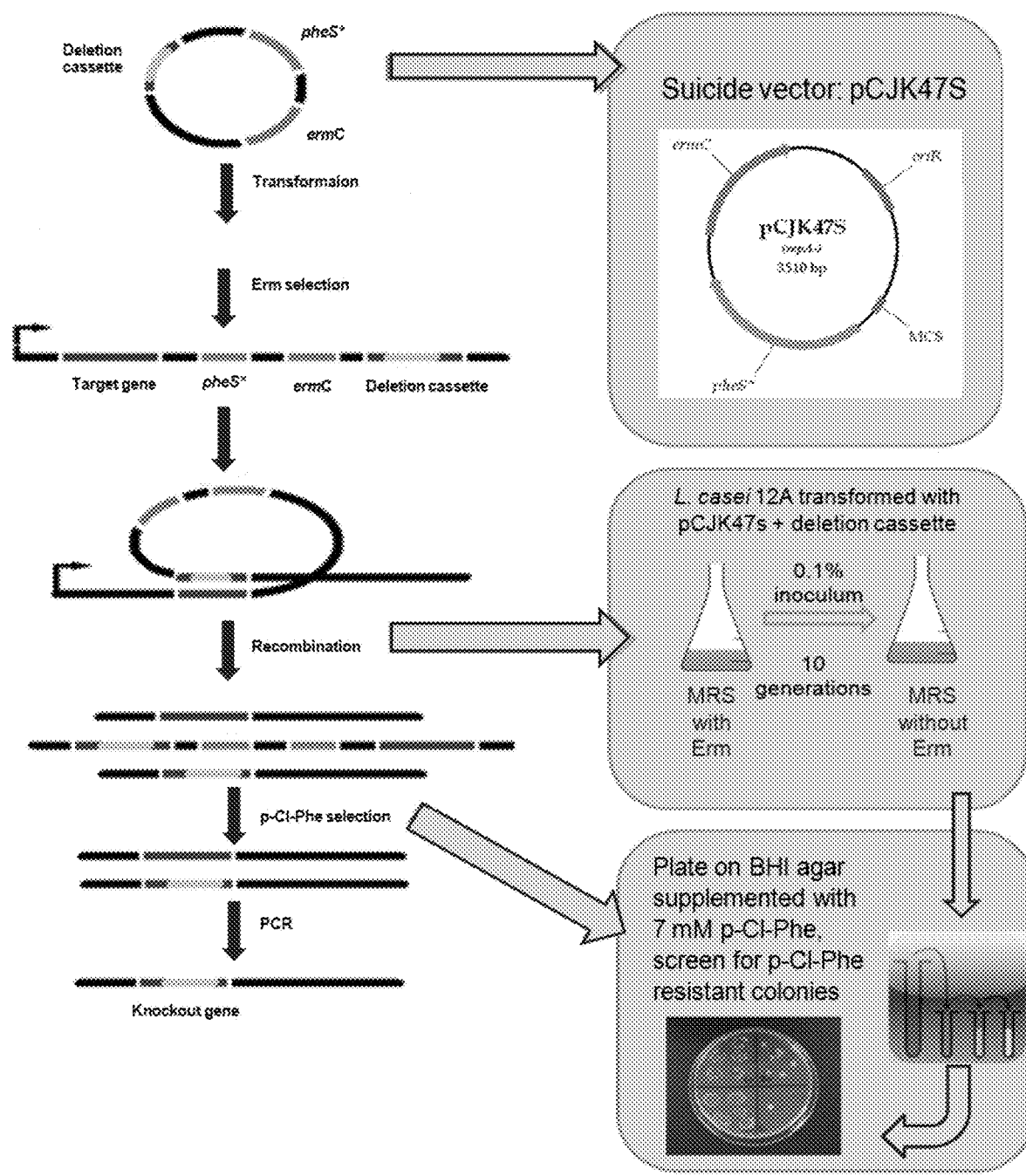
FIG. 4. Schematic illustrating the gene replacement procedure developed for gene replacement in *L. casei* 12A. Presence of the pheS* loci results in sensitivity to p-Cl-Phe. This phenotype (derivatives with pheS* form smaller colonies) allows for selection derivatives that have undergone recombination resulting in loss of the pheS* loci (derivatives without phe* form bigger colonies).
Figure 5A:
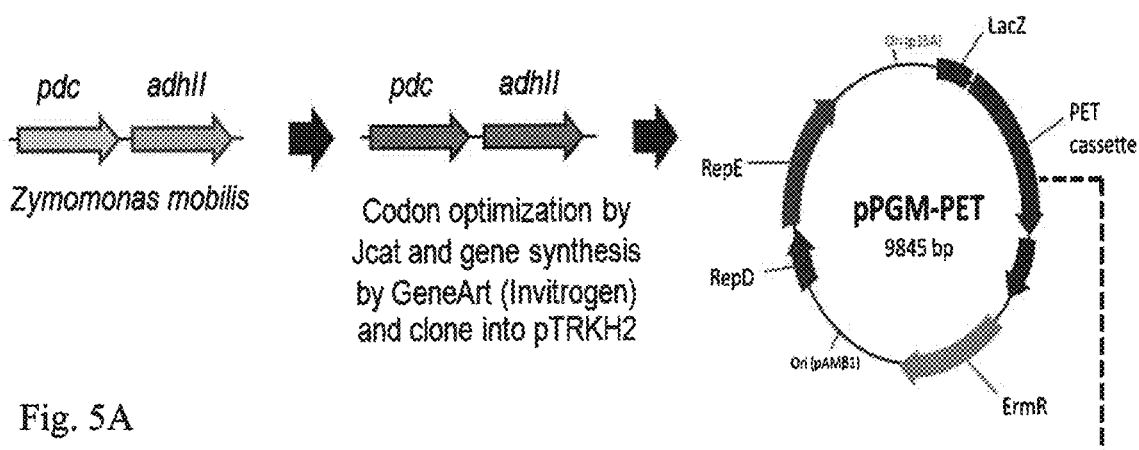
FIG. 5A. Construction of PET cassette in pTRKH2. PET cassette sequence was obtained from *Zymomonas mobilis*. Codon usage of pdc and adhII were optimized specifically for *L. casei* 12A using Java Codon Adaptation Tool (Jcat). Codon optimized cassette was synthesized then cloned into pTRKH2 for expression in *L. casei* 12A.
Figure 5B:
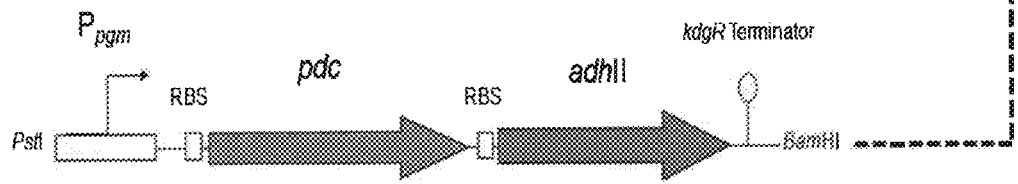
Figure 6:
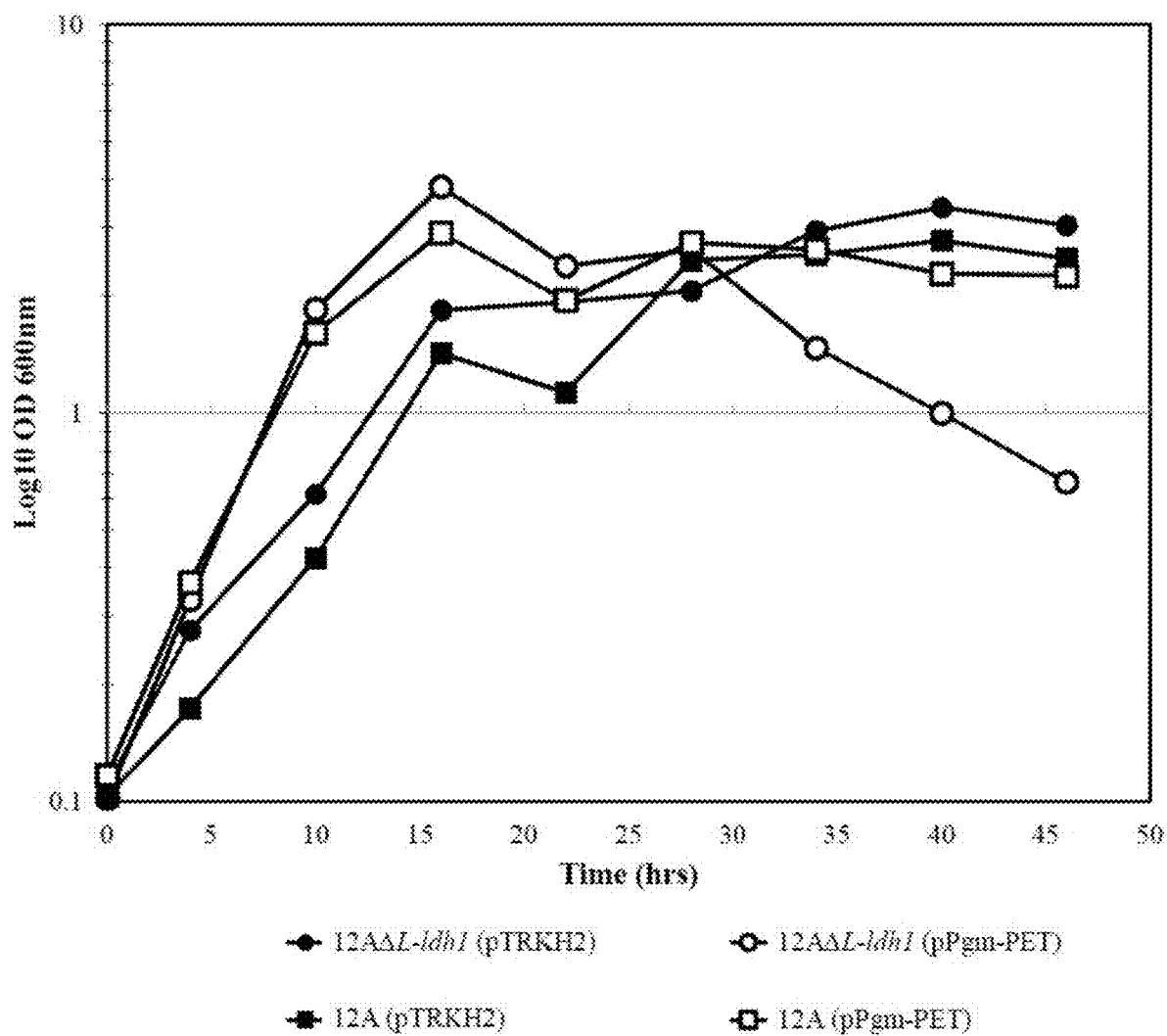
FIG. 6. Growth curves of *L. casei* 12A and 12A Δldh1 transformed with empty pTRKH2 (control) or pPgm-PET growth in chemically defined medium (CDM) for 48 hrs. Working cultures were prepared from frozen stocks by two sequential transfers in MRS broth (see J. C. de Man, M. Rogosa and M. Elisabeth Sharpe, Appl. Bact. 23. 130-135 (1960)) with incubations conducted statically at 37° C. for 24 hrs and 18 hrs, respectively. These cultures were then transferred to mCDM overnight and monitored every 6 hrs for OD600 (optical density at 600 nm).

The general strategy that was used to redirect metabolic flux in *L. casei* 12A from lactic acid to ethanol is illustrated in detail in FIG. 3. Two different methods were used to carry out the strategy. The first method, involving gene deletion, is illustrated in FIG. 4. The second method, involving the construction and subsequent expression of a synthetic PET expression cassette construct in pTRKH2, is illustrated in FIG. 5. The growth of the resulting *L. casei* 12A ethanologens in Chemically Defined Medium (CDM) is illustrated in FIG. 6. The fermentation by-products of the *L. casei* mutants grown in CDM were measured, and the results are shown in Table 6.

TABLE 6

Fermentation products of *L. casei* 12A and mutants with and without pTRKH2 or pPGM-PET growth in CDM for 48 hrs.

| Derivative | Ethanol (%) | L-Lactate (%) | D-Lactate (%) |
|---|---|---|---|
| 12A | 0.0 | 95.0 | 5.0 |
| 12A ΔL-ldh1 | 6.0 | 49.0 | 45.0 |
| 12A ΔL-ldh2 | 0.0 | 96.0 | 4.0 |
| 12A ΔD-hic | 0.0 | 71.0 | 29.0 |
| 12A ΔL-ldh1ΔL-ldh2 | 14.0 | 34.0 | 52.0 |
| 12A(pTRKH2) | 0.0 | 95.0 | 5.0 |
| 12A(Ppgm-PET) | 61.0 | 34.0 | 1.0 |
| 12A ΔL-ldh1(pTRKH2) | 13.0 | 47.0 | 40.0 |
| 12A ΔL-ldh1(Ppgm-PET) | 90.9 | 1.5 | 1.5 |

Note:
*L. casei* 12A mutants were grown in MRS from glycerol stock for 24 hrs at 37° C. then transferred to MRS and incubated for an additional 18 hrs. CDM containing 50 mM glucose was inoculated and incubated in GC vials for 48 hrs at 37° C. At the 48-hr time point, supernatant was drawn off and submitted to GLBRC enabling technologies for fermentation by-product analysis via HPLC-RID.

Conclusions.

Inactivation of L-Ldh1 reduced flux towards L-lactate and enhanced flux towards D-lactate and ethanol. Inactivation of L-Ldh2 and L-Lhd3 increased these changes in metabolic flux.

In *L. casei* 12A with the PET cassette, ethanol made up 61% of metabolic end products formed, while 91% of metabolic end productions were directed to ethanol when the PET cassette was introduced into *L. casei* 12A ΔL-ldh1.

The multi-pronged strategy, inactivating genes encoding enzymes that produce lactic acid or mannitol and introducing the PET cassette, effectively converted *L. casei* 12A from producing lactate as its main metabolic product to producing ethanol as its main metabolic end product.

REFERENCES

Cai, H., Thompson, R. L., Broadbent, J. R., and Steele, J. L. (2009). Genome Sequence and Comparative Genome Analysis of *Lactobacillus casei*: Insights into their niche-associated evolution. Genome Biol. and Evol. 1:239-257.

Duong, T., Miller, M. J., Barrangou, R., Azcarate-Peril, M. A., and Klaenhammer, T. R. (2010). Construction of vectors for inducible and constitutive gene expression in *Lactobacillus*. Microbiol Biotech, 4(3): 357-367.

Kristich, C. J., Chandler, J. R., and Dunny, G. M. (2007). Development of a host-genotype-independent counterselectable marker and a high-frequency conjugative delivery system and their use in genetic analysis of *Enterococcus faecalis*. Plasmid 57:131-144.

Example E. Use of an Alternate Promoter

In the previous examples, a first generation *Lactobacillus casei* ethanologen was created by a two pronged approach to redirect metabolic flux in *L. casei* 12A from lactate to ethanol. The first prong was to inactivate genes encoding lactate dehydrogenases, enzymes which compete with the 12A pathway to ethanol. The second prong was the introduction of synthetic genes modeled from *Zymomonas mobilis* that encode pyruvate decarboxylase (Pdc) and alcohol dehydrogenase II (Adh2) activities (PET cassette). These genes were designed utilizing the *L. casei* codon usage for highly expressed genes and placed under the control of *L. casei* phosphoglycerate mutase promoter, thought to be a constitutively expressed promoter.

This approach was highly successful, resulting in a strain that utilized 504.5 mM glucose (9.1%) glucose in 96 h and produced 934.7 mM of "pyruvate-derived" metabolic end products, which is 92.6% of the theoretical yield from 504.5 mM glucose in a 500 ml fermentation vessel under anaerobic conditions at 37° C. in a defined media with 540 mM glucose. Ethanol was produced at a level of 771.3 mM (4.5%), which was 82.5% of the metabolic end-products. The second most abundant metabolic end product was mannitol which was present at 110.1 mM after 96 h.

Mannitol accumulation began at approximately 21 h. At the same time, ethanol as a percentage of the total metabolic end products began to decrease (% ethanol in total), suggesting that pyruvate decarboxylase activity becomes limiting at that time. This corresponds to the entry of this organism into stationary phase, suggesting that the *L. casei* phosphoglycerate mutase (pgm) promoter used to drive expression of the PET cassette is poorly expressed in stationary phase. Mannitol accumulation was overcome by inactivation of the two mannitol dehydrogenase genes and the introduction of a second copy of the PET cassette under the control of the UspAC2 promoter. This derivative is designated *Lb. casei* E3.

REFERENCES

Lee, S. G., K. W. Lee, T. H. Park, J. Y. Park, N. S. Han, and J. H. Kim. 2012. Proteomic analysis of proteins increased or reduced by ethanol of *Lactobacillus plantarum* ST4 isolated from makgeolli, traditional Korean rice wine. J. Microbiol. Biotechnol. 22:516-525.

Example F. Native Promoters with PET in *Lactobacillus casei* 12A ΔL-ldh1

To determine if the level and timing (growth phase) of expression *L. casei* pgm, groEL, dnaK and uspAC2 promoters impacted ethanol production these promoters were placed in front of the PET cassette and introduced into *L. casei* 12A ΔL-ldh. These strains were grown in 5 ml MRS broth containing 2.5 µg/ml erythromycin (Erm) at 37° C. for 24 h. Then the cultures were transferred into 5 ml CHILL medium with 50 mM glucose and 25 µg/ml Erm and continued to grow at 37 C for 24 h. The composition of these media is included as supplementary material. These cultures were washed twice with saline solution (0.85% NaCl) and resuspended in complete synthetic corn stover hydrolysate (SynH) containing 2.5 µg/ml Erm. The $OD_{600}$ in all cultures was adjusted to 0.1 and then 1 ml aliquots of each culture were transferred into 2 ml GC vials. In each vial, the septum on the cap was pierced by a needle (25G, 0.5 inches). This was done to prevent headspace pressure build up in the vial during fermentation. Samples were incubated at 37° C. for 96 h. For each time point, cells were removed by centrifugation and the supernatants were filtered through 0.2 µm syringe filters and subjected to HPCL analysis to identify metabolic end products. Two biological replications each with two technical replications were conducted.

The results of this analysis are presented in Table 7. These clearly demonstrate that the $pP_{uspA}$ results in the production of significantly (p<0.05) more ethanol than any of the other promoters examined. In stationary phase (hours 48 to 96) $pP_{uspA}$ and $pP_{pgm}$ produce 77.3 and 60.4 mM, respectively. This promoter was then utilized to drive expression of a second copy of the PET cassette thereby reducing the accumulation of mannitol.

TABLE 7

Fermentation end products of *L. casei* 12A ΔL-ldh1 containing plasmids with the PET cassette under the control of different native promoters

| Plasmid | Time (h) | Fermentation end products, mM[a] | | | | Ethanol produced in stationary phase*[b] |
|---|---|---|---|---|---|---|
| | | Lactate | Acetate | Acetoin | Ethanol | |
| $pP_{pgm}$-PET | 12 | 1.3 ± 0.4 | 4.3 ± 0.7 | BQL[c] | 22.3 ± 0.1 | 60.4 |
| | 24 | 6.2 ± 0.8 | 4.2 ± 0.8 | 0.4 ± 0.3 | 68.0 ± 5.0 | |
| | 48 | 10.8 ± 0.3 | 5.5 ± 0.0 | 0.7 ± 0.1 | 137.2 ± 1.7 | |
| | 72 | 13.9 ± 0.7 | 6.2 ± 0.5 | 0.7 ± 0.0 | 187.8 ± 4.1 | |
| | 96 | 14.9 ± 1.6 | 5.6 ± 0.5 | 0.9 ± 0.0 | 197.6 ± 2.9 | |
| $pP_{groEL}$-PET | 12 | 3.4 ± 0.1 | 4.6 ± 0.1 | BQL | 15.8 ± 0.4 | 47.6 |
| | 24 | 10.3 ± 0.1 | 2.0 ± 0.1 | 0.6 ± 0.0 | 46.7 ± 0.4 | |
| | 48 | 27.4 ± 1.8 | 0.7 ± 0.7 | 1.1 ± 0.2 | 100.9 ± 4.7 | |
| | 72 | 36.3 ± 2.2 | 1.6 ± 1.1 | 1.3 ± 0.1 | 138.2 ± 9.0 | |
| | 96 | 38.2 ± 0.2 | 2.1 ± 1.5 | 1.7 ± 0.3 | 148.5 ± 3.9 | |
| $pP_{dnaK}$-PET | 12 | 2.1 ± 0.5 | 2.8 ± 0.1 | BQL | 8.7 ± 2.7 | 24.7 |
| | 24 | 10.6 ± 0.3 | 2.9 ± 0.0 | 0.9 ± 0.0 | 31.0 ± 0.3 | |
| | 48 | 31.6 ± 0.2 | BQL | 2.0 ± 0.2 | 78.0 ± 3.1 | |
| | 72 | 38.5 ± 4.6 | BQL | 2.3 ± 1.3 | 98.5 ± 5.8 | |
| | 96 | 41.7 ± 6.6 | BQL | 2.4 ± 2.8 | 102.7 ± 14.4 | |
| $pP_{hypo}$-PET | 12 | 1.1 ± 0.5 | 2.1 ± 0.6 | 0.2 ± 0.6 | 9.1 ± 1.8 | 27.3 |
| | 24 | 7.9 ± 1.3 | 4.6 ± 0.4 | 0.7 ± 0.4 | 23.9 ± 4.1 | |
| | 48 | 31.6 ± 1.0 | BQL | 2.7 ± 0.2 | 68.2 ± 3.6 | |
| | 72 | 44.4 ± 2.2 | BQL | 3.1 ± 0.5 | 88.0 ± 1.9 | |
| | 96 | 49.4 ± 1.5 | BQL | 3.2 ± 0.6 | 95.2 ± 3.6 | |
| $pP_{uspA}$-PET | 12 | 4.7 ± 3.3 | 2.4 ± 1.3 | BQL | 14.1 ± 1.4 | 77.3 |
| | 24 | 12.5 ± 0.2 | 5.9 ± 0.3 | 0.5 ± 0.0 | 54.6 ± 5.8 | |
| | 48 | 22.4 ± 1.0 | 5.7 ± 0.5 | 0.6 ± 0.0 | 132.1 ± 2.5 | |
| | 72 | 30.3 ± 1.9 | 4.7 ± 2.3 | 0.7 ± 0.0 | 192.0 ± 2.2 | |
| | 96 | 32.3 ± 3.0 | 3.9 ± 0.1 | 0.8 ± 0.0 | 209.4 ± 3.9 | |
| pTRKH2 | 12 | 3.50 ± 0.7 | 3.0 ± 1.1 | BQL | 6.1 ± 0.3 | 6.3 |
| | 24 | 7.7 ± 0.9 | 4.4 ± 1.1 | BQL | 7.1 ± 2.1 | |
| | 48 | 37.1 ± 6.0 | BQL | 2.4 ± 0.4 | 16.4 ± 4.2 | |
| | 72 | 64.4 ± 0.9 | BQL | 3.4 ± 0.0 | 24.7 ± 1.3 | |
| | 96 | 72.7 ± 1.4 | BQL | 3.7 ± 0.3 | 22.6 ± 0.7 | |

[a]Values are averages ± standard deviation.
[b]Percent by w/v
[c]BQL = Below quantitative limit Example G. The Use of Bacteriocin-Producing Lactic Acid Bacteria Ethanologens to Control Contaminants in Biofuel Plants Bacteriocins produced by LAB may display narrow or broad range of target species. For example, nisin, a lantibiotic produced by some strains of *Lactococcus lactis*, and Class II bacteriocins such as pediocin and brochocin, which are made by strains of pediococci, lactobacilli, and *Brochothrix campestris*, each display broad inhibitory activity against a variety of LAB spoilage microbes in alcoholic fermentations.

This example describes converting *Lactobacillus casei* 12A to an ethanologen with the ability to express bacteriocins in lactic acid bacteria (LAB), including *Lb. casei* 12A. The bacteriocins produced by the inventors' constructs allow the inventive ethanologens to inhibit contaminating lactic acid bacteria (LAB) in ethanol plants, thereby reducing the production of lactate/acetate and enhancing ethanol yield. This methodology allows the reduction of lactate/acetate losses without the use of antibiotics.

Experimental Approach and Results

Construction and Cloning of Genes Encoding Pediocin Production.

Figure 7:
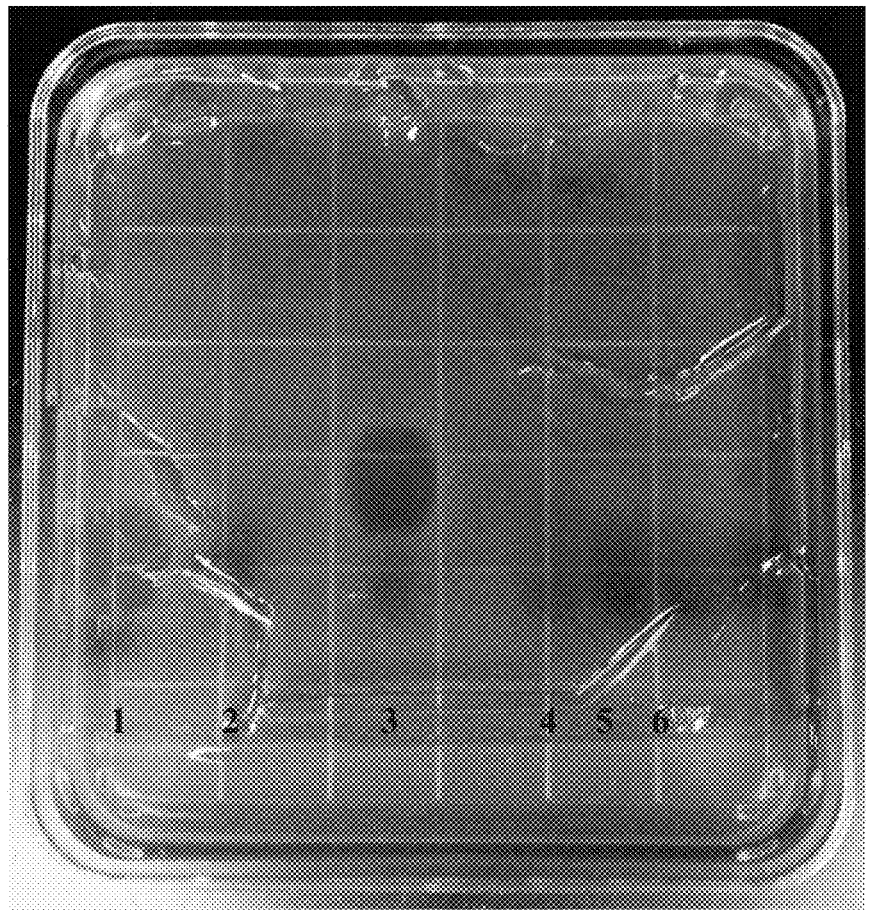
FIG. 7. SDS-PAGE agar overlay bacteriocin inhibition assay using concentrated supernatants. Lane 1, 50 ng of pediocin standard; Lane 2, *Lb. casei* E2 (pNZ8048); Lane 3, *Lb. casei* E2 pNZPed+.
Figure 8:
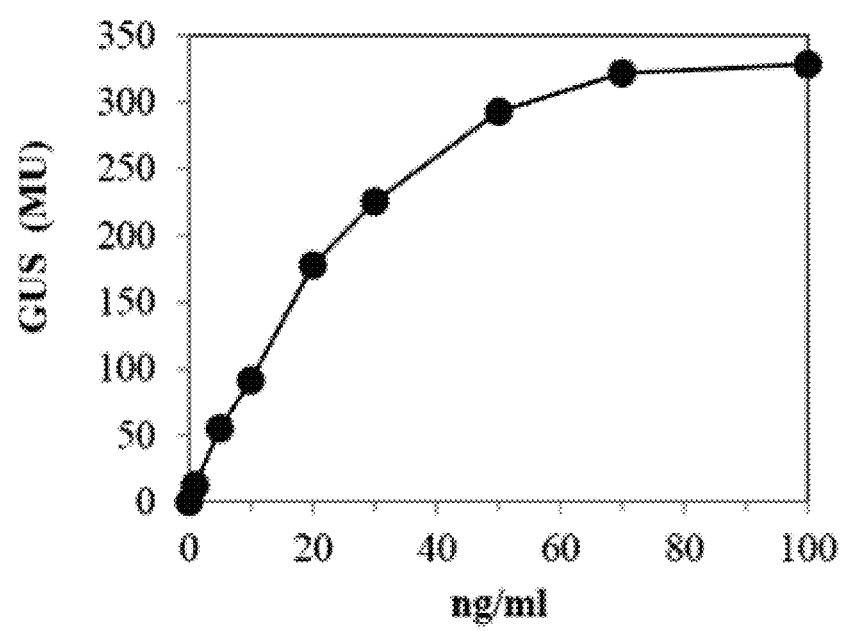
FIG. 8. Inducible GusA expression by *L. casei* in response to different levels of sakacin AIP.

The sequence of the entire gene cluster required for the production of pediocin (pedABCD) by *Pediococcus acidilactici* PAC 1.0 were obtained from Genbank, codon optimized, and synthesized by GeneArt. These genes were cloned into pNZ8048, a cloning vector demonstrated to be stably maintained without antibiotic selection in *Lactobacillus casei* 12A derivatives, under regulation by promoter Ppgm. The construct was introduced in *Lb. casei* E2 (*Lb. casei* 12A with its three primary lactate dehydrogenases (L-ldh1, L-ldh2, and D-hic) inactivated and which contains the production of ethanol cassette). This construct, designated *Lb. casei* E2 (pNZPed+) and the corresponding control strain *Lb. casei* E2 (pNZ8048) were grown in MRS broth to stationary phase. Culture supernatants were freeze-dried and resuspended in 10% of the original volume in sterile water. The concentrated supernatants from these cultures and a pediocin control (Sigma) were mixed with Tricine sample buffer with β-mercaptoethanol (Biorad) at 1:1 volume and heated at 95° C. for 5 min before loading into 10-20% Tricine SDS-PAGE (Biorad). After electrophoresis, the gels were washed with sterile water overnight at 4° C., placed on MRS$_{erm}$ agar and overlaid with 20 ml MRS$_{erm}$ soft agar containing approximately 2×10$^6$ CFU of *Enterococcus faecalis* CKIII. The plates were in incubated at 37° C. until cell growth was detected. The results of this analysis are shown in FIG. 7. While the gel is slightly distorted around the pediocin control, the pediocin-induced zone of clearing from the *Lb. casei* E2 (pNZPed+) concentrated supernatant is readily apparent.

Screening LAB Isolated from Ethanol Plants for Susceptibility to Pediocin or Brochocin.

A variety of microorganisms are known to contaminate bioethanol fermentations, however LAB, particularly lactobacilli, are of primary concern (Beckner et al., 2011). The inventors' laboratory has isolated sixty-two LAB from four ethanol plants in the Midwest region of the United States. This ethanol plant culture collection contains isolates of *Lb. fermentum*, *Lb. plantarum*, *Lb. brevis*, *Lb. mucosae*, *Lb. helveticus*, *Lb. heilongjiangensis*, *Lb. amylovorous*, *Lb. casei*, *Enterococcus* sp. and *Pediococcocus pentosaceus* strains that were gathered from all stages of the ethanol fermentation process. Thirty of these cultures were propagated from frozen by sequential transfers through MRS broth and corn mash extract, a filtrate obtained from corn mash from a bioethanol plant. Pediocin (Sigma) was added at 500 ng/ml to corn mash extract, inoculated with one of the ethanol plant isolates, incubated at 37° C. and growth was monitored by following O.D.$_{600}$. Growth of five of the thirty ethanol plant isolates was inhibited.

Construction and Cloning of Genes Encoding Brochocin Production.

The sequence of the genes required for brochocin production and immunity (brcABC) by *Brochothrix campestris* ATCC 43754 were obtained from Genbank, codon optimized, and synthesized by GeneArt. These genes were cloned into pNZ8048, a cloning vector demonstrated to be stably maintained without antibiotic selection in *Lb. casei* 12A derivatives, under regulation by promoter Ppgm and which included the pediocin transport genes pedCD. The brcABCpedCD construct was introduced in *Lb. casei* E2 (*Lb. casei* 12A with its three primary lactate dehydrogenases (L-ldh1, L-ldh2, and D-hic) inactivated and which contains the production of ethanol cassette. This construct, designated *Lb. casei* E2 (pNZBrc+) and the corresponding control strain *Lb. casei* E2 (pNZ8048) were grown in MRS broth to stationary phase. Culture supernatants were collected, freeze-dried and resuspended in 10% of the original volume in sterile water. Agar diffusion assays of the crude BrcC preparation against LAB isolated from different ethanol plants showed 15 of 18 ethanol plant isolates (which included strains of *Lb. fermentum*, *Lb. plantarum*, *Lb. brevis*, *Lb. mucosae*, *Lb. helveticus*, *Lb. casei* E2 control, *Enterococcus* sp., and *Pediococcocus pentosaceus*) were sensitive to this bacteriocin. Growth studies in a 96-well plate assay with 8 representative ethanol plant isolates showed growth of all 8 strains in MRS medium was either completely (i.e., no growth after 48 h; *Lb. fermentum* A, *Lb. mucosae* 2C2, *Lb. helveticus* 3C2, *Lb. plantarum* 3C3, and *Lb. fermentum* 3C9) or partially (i.e., growth observed after 48 h; *Lb. brevis* C, *Lb. plantarum* WC, and *Pediococcus pentosaceus* 4C0) inhibited by BrcC.

Pediocin and brochocin are known to inhibit a particular range of LAB, and serve as exemplary model bacteriocins. Other bacteriocins with equal or even broader inhibition ranges may be, based on the present disclosure, synthesized and secreted in a similar manner. Table 8 compares the effectiveness of three different LAB bacteriocins against the three antibiotics most commonly utilized in the ethanol industry as well as another industry antimicrobial ingredient, hop acids. The analyses were conducted in corn steep liquor broth at 33° C. and pH 5.0, which represent conditions that mimic those present in bioethanol fermentations. Fifteen strains representative of the organisms isolated from corn ethanol plants were utilized. Antibiotics and hop acids were utilized at the concentrations suggested by companies selling these products into the bioethanol industry. The bacteriocins were utilized at either levels currently being produced (pediocin), at levels reported by others in the research literature (nisin) using commercially available preparations, or in an assay system that allows for analyzing relatively broad range of concentrations (brochocin inhibition assay by agar diffusion). Results demonstrate that brochocin and nisin have spectra of inhibition that are similar to that for the antibiotics erythromycin and virginiamycin. Additionally, these bacteriocins have an inhibitory spectrum similar to that of hop acids in the yeast propagation tank and show greatly superior inhibition versus hop acids in the fermentation vessels.

It is also known that bacteriocins often utilize the same transport systems. Accordingly, the present methodology facilitates the generation of *Lb. casei* derivatives that secrete bacteriocins possessing a broader spectrum of inhibition. Such inhibition reduces the production of lactate/acetate and enhancing ethanol yield in ethanol production processes without the use of antibiotics.

TABLE 8

Sensitivity of 15 wild lactic acid bacteria isolated from ethanol plants to different inhibitors in corn steep liquor broth (CSL) at 33° C. and pH 5.5

| Type | Inhibitor | Concentration | Resistant | Sensitive |
|---|---|---|---|---|
| Bacteriocins | Pediocin | 500 IU/mL[a] | 67% | 33% |
|  | Brochocin | Agar Diff[b] | 9% | 91% |
|  | Nisin | 500 ng/mL[c] | 13% | 87% |
| Antibiotics | Penicillin | 6 µg/mL | 33% | 77% |
|  | Virginiamycin | 3 µg/mL | 13% | 87% |
|  | Erythromycin | 1 µg/mL | 7% | 93% |
| Hop acids | Hop YPT[d] | 25 ppm | 13% | 87% |
|  | Hop Ferm[d] | 1.5 ppm | 87% | 13% |

[a]Pediocin at concentraiion produced by *Lb. casei* E3 (pNZPed+).
[b]Assays done using an agar diffusion assay using crude brochocin prep (freeze-dried supernatant from overnight culture of *Lb. casei* E2 (pNZBrc+). Allows for evaluation of higher concentrations than CSL broth assays
[c]Nisin at levels attainable utilizing cultures of *Lactococcus lactis*.
[d]The concentration of hop acids suggested by the manufacturer for use in the yeast propagation tank (YPT) or the concentration that would be present in the fermenter after fill (Ferm).

A model system was developed to directly evaluate the ability of engineered LAB such as *Lb. casei* E3 (pNZPed+) to inhibit yield reducing bacteria (YRB) in ethanol plants and increase ethanol yields. The model utilizes corn mash prepared from industrial liquefact as the fermentation substrate and simulates the addition of a LAB bacteriocin-producing ethanologen at the time an industrial fermenter starts to be filled with mash. The liquefact is pasteurized by heating in a water bath at 75° C. for 60 min prior to being utilized to reduce the level of contaminants in the corn mash. The experiment is started by adding a sufficient quantity of YRB to reach a level of $1\times10^5$ CFU/g in the corn mash (cooled liquefact), as this bacterial load is typical of that present in industrial corn mash. A quantity equal to 20% of the desired final amount of corn mash containing YRB (i.e., 10 g) is added to a 125 ml Erlenmeyer flask. *Lb. casei* E3 (pNZPed+) is added to the flask at a level that represents 1% of the final volume (i.e., 0.5 ml), resulting in the initial mash having approximately $5.0\times10^7$ CFU/g of *Lb. casei* E3 (pNZPed+). The inoculated mash is incubated at 33° C. statically. Subsequently, additional 20% aliquots (i.e., 10 g) of the contaminated mash ($1\times10^5$ CFU/g of the YRB) are made every 2 hours until the final volume (i.e., 50 g) is attained, 8 h after the start of the experiment. The yeast strain such as "Ethanol Red" is added at hour 8 at a level of $1\times10^8$ CFU/g, followed by addition of an enzyme mix (Distillase CS, DuPont Inc.) to reach 0.35 glucoamylase units/g DS of corn mash and sufficient urea to reach 500 ppm. Incubation is continued at 33° C. for an additional 64 h (total time is 72 h) with mixing (150 rpm for 3 min) every 24 h. The yeast addition is later than would occur in an industrial fermentation, however our preliminary results indicate that the 8 hour incubation is required to observe consistent detectable levels of lactate production. After 72 hours, samples are drawn for pH and HPLC analysis.

Figure 10:
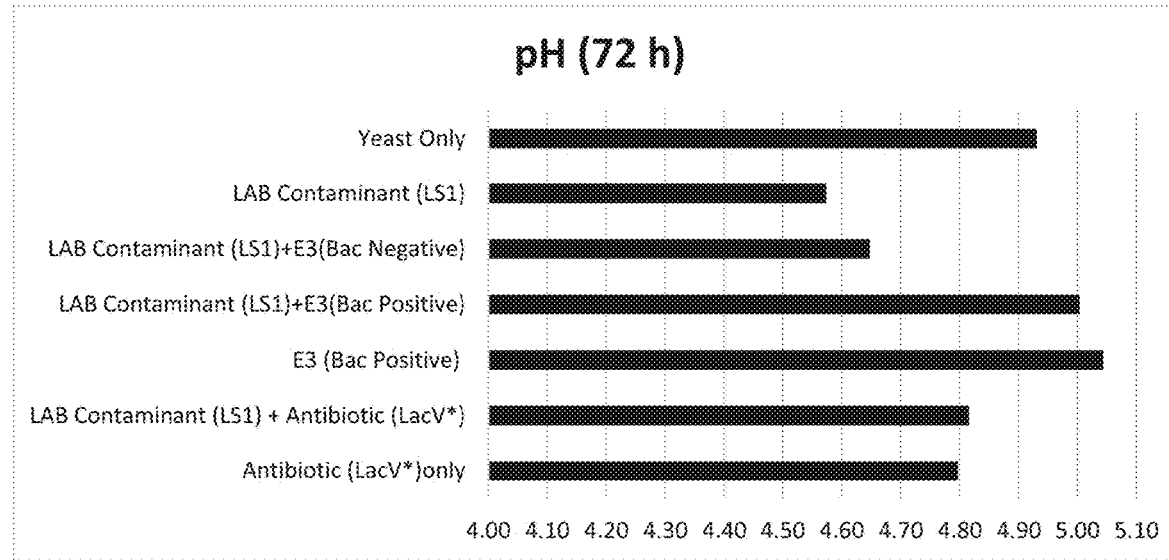
FIG. 10. Changes in pH after 72 h in model ethanol fermentations with *Lb. casei* E3 (pNZPed+; "Bac Positive"), the non-bacteriocin producing *Lb. casei* E3 control ("Bac Negative"), and the yield reducing bacterium *Lb. plantarum* LS1.

The pH at the end of the fermentation is an early indication of the ability of a LAB bacteriocin-producing ethanologen such as LAB such as *Lb. casei* E3 (pNZPed+) to inhibit YRB such as *Lactobacillus* strain LS1. As shown in FIG. 10, the yeast only fermentation resulted in a pH of 4.93, and addition of the YRB strain LS1 results in a pH drop of 0.36 units. Addition of a commonly used antibiotic (LacV) reduced but did not eliminate the drop in pH. In contrast, addition of *Lb. casei* E3 (pNZPed+) to a yeast plus LS1 fermentation stopped the decline in pH. Addition of the non-bacteriocin producing *Lb. casei* E3 control (Bac Negative) did not stop the YRB mediated pH decline. These results demonstrate that bacteriocin production by E3 was effective in stopping the YRB mediated pH decline.

Figure 11:
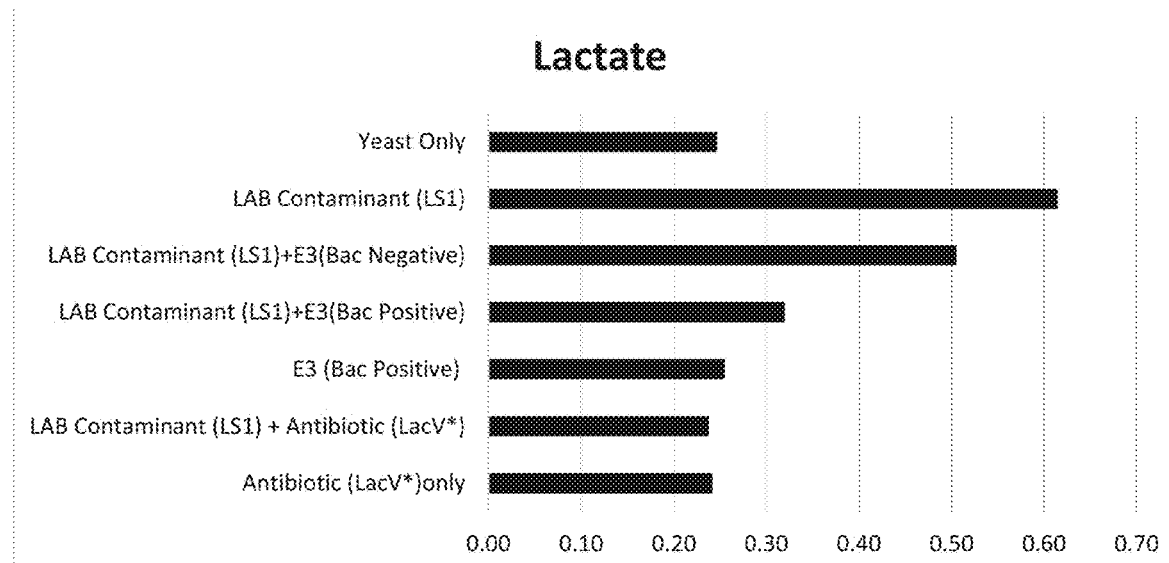
FIG. 11. Lactate levels (w/v) after 72 h in model ethanol fermentations using *Lb. casei* E3 (pNZPed+; "Bac Positive"), the non-bacteriocin producing *Lb. casei* E3 control ("Bac Negative"), and the yield reducing bacterium *Lb. plantarum* LS1.

The decrease in pH that is observed with addition of YRB to the model is indicative of lactate and acetate production. The presence of these organic acids at the end of fermentation represents lost carbon that could instead have been converted to ethanol. Data for lactate levels from the model trials are presented in FIG. 11. The yeast only fermentation contained 0.25% (w/v) lactate at the end of fermentation. Addition of the YRB LS1 resulted in an increase in lactate concentration up to 0.62% (w/v) lactate. The addition of *Lb. casei* E3 (pNZPed+) to a yeast+LS1 fermentation resulted in a lactate concentration of 0.32% (w/v). Thus, *Lb. casei* E3 (pNZPed+) inhibited approximately 75% of the lactate production by LS1, and was nearly as effective as the antibiotic LacV. This effect was not observed with the non-bacteriocin producing *Lb. casei* E3 control (Bac Negative), which confirms that the bacteriocin produced by *Lb. casei* E3 (pNZPed+) is responsible for inhibition of lactate production by LS1.

Figure 12:
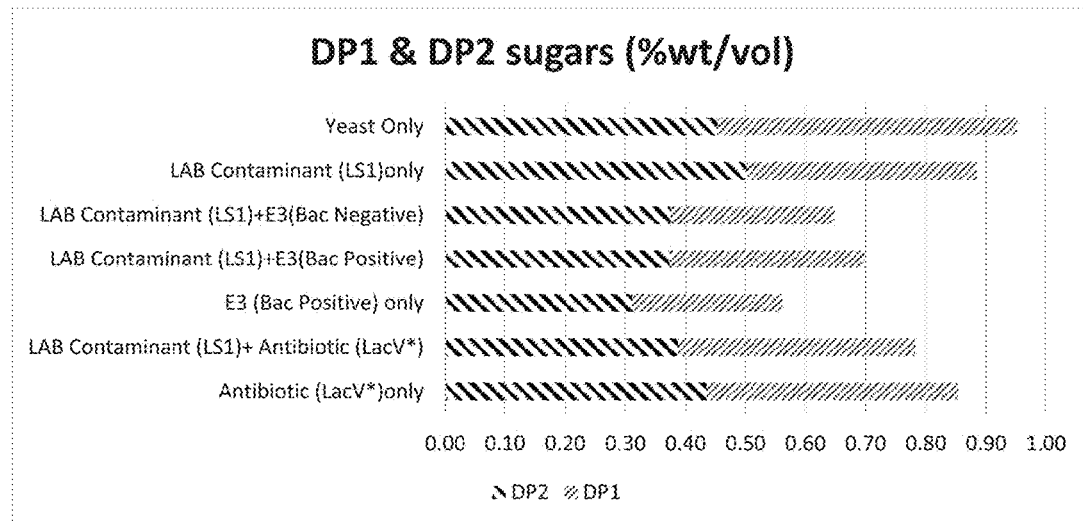
FIG. 12. Final levels (w/v) of DP1 and DP2 carbohydrates after 72 h in model ethanol fermentations using *Lb. casei* E3 (pNZPed+; "Bac Positive"), the non-bacteriocin producing *Lb. casei* E3 control ("Bac Negative"), and the yield reducing bacterium *Lb. plantarum* LS1.

Carbon present in carbohydrates with a degree of polymerization 1 (DP1; i.e., glucose) and degree of polymerization 2 (DP2; i.e., maltose) holds significantly higher value as ethanol than in dried distiller grains with solubles, yet are not converted to ethanol by yeast. Thus, the sugar represented by DP1 and DP2 "peaks" after fermentation represent lost carbon that could be converted to ethanol by a LAB bacteriocin-producing ethanologen such as LAB such as *Lb. casei* E3 (pNZPed+). Data for residual DP1 and DP2 levels from the model fermentations are presented in FIG. 12. The yeast only and yeast plus YRB (strain LS1) fermentations contained 0.95 and 0.89% (w/v) DP1/DP2 at the end of fermentation, respectively. However, addition of *Lb. casei* E3 (pNZPed+) or non-bacteriocin producing E3 (Bac Negative), to a yeast+LS1 fermentation decreased DP1+DP2 levels to 0.70% or 0.65% (w/v) at the end of fermentation, respectively. Additionally, when *Lb. casei* E3 (pNZPed+) alone was added with the yeast, the DP1/DP2 level at the end of fermentation fell to 0.56% (w/v). These results show *Lb. casei* E3 derivatives consumed approximately 0.20% (w/v) of the carbohydrates in the DP1 and DP2 "peaks" that are either not naturally or preferentially utilized by the yeast.

Figure 13:
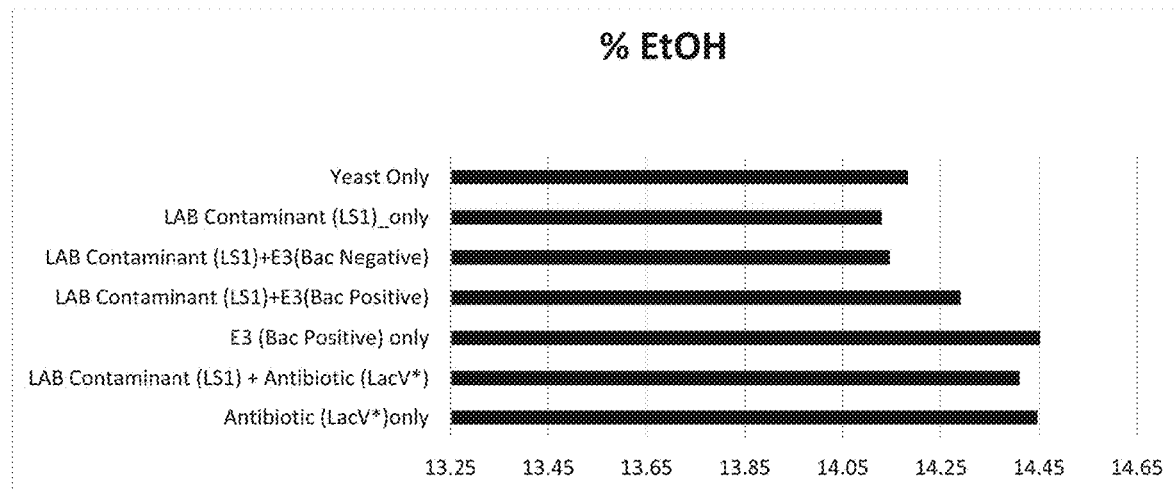
FIG. 13. Ethanol yields (percent, w/v) after 72 h in model ethanol fermentations using *Lb. casei* E3 (pNZPed+; "Bac Positive"), the non-bacteriocin producing *Lb. casei* E3 control ("Bac Negative"), and the yield reducing bacterium *Lb. plantarum* LS1.

The primary objective of corn mash fermentations is the production of ethanol, and ethanol yield data from the model fermentations are shown in FIG. 13. The yeast only and yeast plus YRB (LS1) fermentations contained 14.18 and 14.13% (w/v) ethanol at the end of fermentation, respectively; for an average of 14.16% (w/v) ethanol. Addition of *Lb. casei* E3 (pNZPed+) to either a yeast only or yeast+LS1 fermentations resulted in 14.29 and 14.45% (w/v) ethanol, respectively, for an average of 14.37% (w/v) ethanol. Thus, addition of *Lb. casei* E3 (pNZPed+) increased ethanol yield by approximately 0.2% (w/v). Collectively, results from the model fermentations (Figures A-D) demonstrate that a LAB bacteriocin-producing ethanologen such as *Lb. casei* E3 (pNZPed+) can enhance ethanol production efficiency by inhibiting bacterial contaminants without the use of antibiotics, and by increasing the total sugars that are converted to ethanol.

Example H. Heterologous Expression of Bacteriocins that Inhibit Yield-Reducing Lactic Acid Bacteria from Ethanol Plants Rewiring *L. casei* 12A for ethanol production. To demonstrate the potential of *L. casei* as a robust biocatalyst, we redirected metabolic flux in 12A from lactate to ethanol (Vinay-Lara at al. 2016). Briefly, multiple strategies were pursued concurrently to redirect *L. casei* 12A fermentation to ethanol; first, we inactivated enzymes that consume pyruvate under anaerobic conditions without producing ethanol, including: the D-lactate dehydrogenase (Ldh); four L-Ldhs; D-hydroxyisocaproate dehydrogenase (D-Hic); acetolactate synthase (Als); and oxaloacetate decarboxylase (Oad) using the pCJK47-based system we recently described [70]. 12A derivatives with altered metabolic end product profiles are presented in Table 8.

TABLE 8

Metabolic end products formed by *L. casei* 12A and derivatives during growth in a chemically defined, glucose-media at 37° C., reported as % of total.

| Derivative | EtOH | D-Lac | L-Lac | Ac |
| --- | --- | --- | --- | --- |
| Wild type | 0.8 | 2.9 | 93.3 | 3.1 |
| ΔL-ldh1 | 9.2 | 54.6 | 36.2 | BQL |
| ΔD-Hic | 0.6 | 0.1 | 96.3 | 3.1 |
| ΔL-ldh1/ΔL-ldh2 | 5.4 | 87.5 | 5.5 | 1.5 |
| ΔL-ldh1/ΔD-Hic | 8.3 | 1.8 | 89.8 | BQL |
| ΔL-ldh1/ΔL-ldh2/ΔD-Hic | 11.3 | 2.8 | 52.1 | 33.8 |
| 12A(pLc_P$_{pgm}$-PET) | 10.7 | 9.2 | 78.5 | 1.6 |
| ΔL-ldh1(pLc_P$_{pgm}$-PET) | 71.7 | 15.4 | 7.8 | 5.0 |
| ΔL-ldh1/ΔL-ldh2/ΔD-Hic (pLc-P$_{pgm}$-PET) | 90.2 | 0.8 | 3.1 | 5.9 |
| ΔL-ldh1::P$_{pgm}$-PET[12A E1] | 48.9 | 31.2 | 12.4 | 7.6 |
| ΔL-ldh2/ΔD-Hic, ΔL-ldh1::P$_{pgm}$-PET[12A E2] | 81.6 | 1.1 | 8.0 | 9.2 |

BQL = Below Quantifiable Level.
Abbr: ETOH-ethanol, Lac-lactate, Ac-acetate.

The second strategy involved introduction of a *L. casei* codon-optimized "PET" cassette comprised of the *Z. mobilis* genes [71] for pyruvate decarboxylase (Pdc) and alcohol dehydrogenase (Adh2) under the control of the *L. casei* 12A phosphoglycerate mutase promoter (ppgm). Ppgm has been reported to be a strong, constitutive in *Lactobacillus* species [72,73]. The PET cassette (Lc Ppgm-PET) was ligated into a copy number vector, pTRKH2 [74], to produce pLc_Ppgm-PET, and introduced into various 12A derivatives. The metabolic end product profiles of key 12A derivatives are presented in Table 8. Additionally, the Lc Ppgm-PET cassette was integrated into the 12A ΔL-ldh1 loci of 12AΔL-ldh1 and 12AΔL-ldh1ΔL-ldh2ΔD-hic, these derivatives were designated 12AE1 and 12AE2, respectively. The metabolic end product profiles of these derivatives are also shown in Table 8. These results demonstrate: i) the two approaches are complementary; ii) redirecting metabolic flux in *L. casei* from lactate to an alcohol can be readily achieved; and iii) the plasmid-borne Lc Ppgm-PET cassette was more effective at redirecting metabolic flux than the chromosomally integrated Lc Ppgm-PET cassette, suggesting gene dose is important.

The organism described above was determine to accumulate mannitol under high carbohydrate loading. Mannitol accumulation was overcome by inactivation of the two mannitol dehydrogenase genes and the introduction of a second copy of the PET cassette under the control of the UspAC2 promoter. This derivative is designated *Lb. casei* E3.

Construction of a *L. casei* 12AE2 derivative capable of growth on xylose. The high level of xylose in plant biomass hydrolysates makes the ability to utilize xylose (Xyl+) a priority in any biocatalyst to be used with these feedstocks [75]. In most bacteria, xylose metabolism is accomplished via conversion of xylose to D-xylulose and then to xylulose 5-phosphate by xylose isomerase (XylA) and xylulose kinase (XylB), respectively [76,77]. In facultatively heterofermentative lactobacilli like *Lb. casei*, the phosphoketolase pathway is utilized to metabolize the xylulose 5-phosphate to a mixture of lactate, ethanol, and acetate [78,79]. In LAB, it is also common for a xylose permease (XylT) to be present in xylose utilization operons [80,81]. To make *L. casei* 12A Xyl+, we synthesized a codon-optimized 4,461 bp cassette encoding xylA and xylB from *L. buchneri*, and xylT from *L. brevis* behind the *L. casei* pgm promoter [82,83]. The xylose cassette was introduced into *L. casei* 12A E2 either on pTRKH2 [74] or integrated into the chromosome in the L-ldh3 locus. The derivative containing the plasmid-borne cassette grew on xylose more rapidly and to a greater final cell density that the 12A E2 derivative with a chromosomal copy of the Xyl cassette, indicating once again that gene copy is important to Xyl+. As the result of removal of catabolite repressive elements, the 12A Xyl+ derivatives co-utilize glucose and xylose and produce ethanol and acetate.

Redirecting flux from the phophoketolase pathway exclusively through pyruvate. *L. casei* utilizes pentose sugars through the phosphoketolase pathway resulting in the formation of equimolar quantities of lactate and acetate [84]. Okano et al. [79] demonstrated it was possible to redirect pentose metabolism through the pentose phosphate pathway in LAB by inactivating the phosphoketolase (xpk) gene via the introduction of a *Lactococcus lactis* transketolase gene within its loci. A similar approach has been applied to *L. casei* 12A E3 and determined to redirect xylose utilization through pyruvate; thereby allowing for higher yields of pyruvate-derived metabolites from pentoses.

Identification of constitutive promoters. A synthetic promoter library was developed in *L. plantarum* that spans 3-4 logs of expression in small increments [85]. This promoter library was also evaluated in *L. sakei* and the level of expression correlated with that observed in *L. plantarum* [85]. To evaluate the activity of these promoters in *L. casei*, ppgm and three *L. plantarum* promoters with medium, medium-high, and high levels of expression were inserted upstream of a gene encoding β-glucosidase (gusA), ligated to pTRKH2 [74], and transformed into *L. casei* 12A E2. The three *L. plantarum* synthetic promoters resulted in the expected medium, medium-high, and high levels of GUS activity, while the pgm promoter gave far lower GUS activity (~10-fold lower than the lowest *L. plantarum* promoter). These results confirm the *L. plantarum* synthetic promoter library will function in *L. casei* and suggest the pgm promoter is rather weakly expressed.

Inducible promoters. Metabolic engineering of LAB has been greatly facilitated by exploitation of an autoregulatory system for nisin production (NICE system), a bacteriocin produced by *Lactococcus lactis* [111], and the 3-component quorum sensing gene cluster for sakacin, a bacteriocin produced by *Lb. sakei* [111]. Characterization of sakacin-like bacteriocin clusters in FHL has demonstrated transcription of the bacteriocin structural gene is activated by interaction between an associated two-component signal transduction system (TCS) and autoinducing peptide (AIP) pheromone [112,113]. More importantly, vectors developed from the *Lb. sakei* AIP system have provided more tightly regulated and highly induced heterologous gene expression than the NICE system in two key FHL species, *L. sakei* and *L. plantarum* [114], and we have successfully deployed this system in *L. casei*. Plasmid pSIP411, which contains β-glucosidase (gusA) under the control of the sakacin inducible promoter [115], was electroporated into *L. casei* 12A E2. GusA expression in response to different levels of synthetic inducer peptide (0-100 ng/ml) displayed a near linear dose response up to 50 ng/ml, with a >300-fold dynamic range (FIG. 1).

Example I. Heterologous Expression of Bacteriocins and Bacteriocin Immunity by a *L. casei* Ethanologen Bioenergy production via fermentation of agricultural feedstocks is increasing worldwide. Bioethanol remains the predominant end product, but commercial manufacture of next generation biofuels such as biobutanol is also expanding. Irrespective of the product, bioenergy production from agricultural feedstocks is regularly subject to microbial contamination which negatively affects process efficiency and profitability. Losses caused by microbial contamination at individual US bioethanol plants, for example, have been estimated at $14.5 million per year (Muthaiyan et al. 2011), and there are over 200 bioethanol plants operating in the US. LAB are the most prominent group of contaminants (Beckner et al. 2011; Murphree et al. 2014; Steele and Broadbent, unpublished results), and cause both chronic and acute infections in the plant (Skinner and Leathers 2004). Chronic infections reduce ethanol yields by siphoning carbon away from yeast (Lucena et al. 2010; Muthaiyan et al. 2011), while acute infections curtail ethanol production by directly inhibiting yeast (Skinner and Leathers 2004). Addition of antibiotics, primarily penicillin and virginiamycin (Muthaiyan et al. 2011), is currently the most common means for control against these loses. As expected, this practice has led to the emergence of antibiotic-resistant contaminants (Murphree et al. 2014), and it may also affect the value of fermentation byproducts such as dried distillers grains with solubles (Bischoff et al. 2016; McChesney 2009). Thus, process improvements that effectively control bacterial contamination would substantially improve the production efficiency and capacity of bioenergy production from agricultural feedstocks.

Figure 9:
FIG. 9. Physical map of gene clusters encoding bacteriocins used as examples in this application. The fill patterns identify ORFs coding the bacteriocin structural gene (black), transport proteins (dark gray), modification or maturation (light gray), immunity (stippled), and other functions (white). Map is not to scale.
Figure 9:
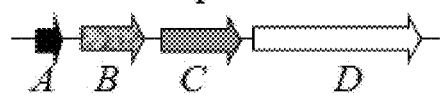
Figure 9:
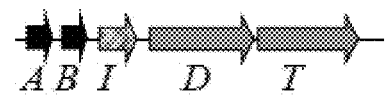
Figure 9:

The four bacteriocins described in this prophetic example are synthesized as pre-peptides with an N-terminal amino acid leader sequence, and secreted via a specific transporter encoded within the gene cluster responsible for bacteriocin production (Bierbaum and Sahl, 2009; McCormick et al. 1998; Papagianni and Anastasiadou, 2009; van Belkum et al. 2010) (FIG. 9). As is illustrated in FIG. 9, these gene clusters also include one or more genes that confer host immunity against the bacteriocin.

For this example, the inventors will create synthetic cassettes for expression of each bacteriocin in *L. casei* E3, and separate cassettes to confer immunity. The cassettes for immunity will be integrated into the chromosome of *L. casei* E3, while those encoding bacteriocin production will be carried on multi-copy plasmids. The coding regions in each cassette will be codon optimized for *L. casei* using the Java Codon Adaptation Tool (JCAT, Technical University Braunschweig Institute for Microbiology) with all annotated *L. casei* 12A genes as the input. As is noted in the preceding examples, we have successfully expressed synthetic pediocin A and brochocin-C gene clusters in *L. casei* E3; this example will focus on nisin and carnocyclin A.

The nisin production (NisP) cassette will include nisA-P genes described in FIG. 9, and the nisin immunity (NisI) cassette will incorporate nisIEFG (Bierbaum and Sahl 2009). nisR and nisK genes will be excluded as they encode a two-component system for regulation of nisin production (Seizen et al. 1996) whose target sequence (the nisA promoter) will not be included in the synthetic construct. Instead, the cassette will be synthesized with the dnaK promoter, which we have found is expressed at a moderate level during all phases of growth (Broadbent et al. 1997).

The NisI cassette will be assembled in a pCJK47 derivative, pBS1, and integrated into the acetolactate decarboxylase (ald) locus of *L. casei* E3. This plasmid is a suicide vector in *L. casei* and has been used for the integration of constructs into the *L. casei* chromosome (Broadbent et al. 2014), and inactivation of ald has been determined to have no impact on growth in media not containing citrate. The *L. casei* NisI construct will be verified by DNA sequence analysis and screened for nisin immunity by the agar overlay method using *Lactococcus lactis* 11454 as the nisin producer (Steele and McKay, 1986).

The NisP cassette is relatively large (~9 kb), and so will be synthesized in four parts and assembled in *L. casei* NisI through sequential cloning in pDW2. The final *L. casei* NisP::NisI construct will be verified by DNA sequence analysis and screened for nisin production and immunity by the agar overlay method using *Lactococcus lactis* LM0230 as the nisin-sensitive indicator (Steele and McKay, 1986).

Synthesis of cassettes for production and immunity of the other bacteriocins will be performed in similar fashion. The production of carnocyclin A (CclP) cassette will include cclBTCDA, and the immunity cassette (CclI) will encode cclIEFGH (van Belkum and Vederas 2012). In each case, the cassette design, use of the chromosomal ald site and plasmid DNA to insert genes encoding immunity and production, respectively, and confirmation of sequence and function will be performed as described for NisP.

The quantity of bacteriocin in the cell-free culture supernatants (filter sterilized) will be determined using a serial dilution method. The cell-free culture supernatants will be diluted in 0.85% saline, 5 mm filters will be saturated with the diluted supernatants, and then placed on MRS soft agar containing different LAB isolated from coren starch ethanol plants. The inventors' laboratory has a bank of more than 150 strains of LAB containing fifteen different species, with the following 10 species being highest in abundance: *Lb. helveticus*, *Lb. amylovorous*, *Lb. fermentum*, *Lb. brevis*, *Lb. casei*, *Lb. plantarum*, *Pediococcus pentosaceus*, *Lactococcus lactis*, *Weissella* sp. and *Enterococcus faecium*. Screening will include one representative strain of the ten species listed above.

This example describes a series of *L. casei* strains that produce one of four different bacteriocins and are immune to all four. The present strategy will enable use of these strains in pairwise combinations that leverage the different modes of action for each bacteriocin to reduce the selective pressure for resistance to any one bacteriocin and lengthen the time that these strains will be effective for the control contaminating bacteria in ethanol plants.

Each reference identified in the present application is herein incorporated by reference in its entirety. While present inventive concepts have been described with reference to particular embodiments, those of ordinary skill in the art will appreciate that various substitutions and/or other alterations may be made to the embodiments without departing from the spirit of present inventive concepts. Accordingly, the foregoing description is meant to be exemplary, and does not limit the scope of present inventive concepts.

We claim:

1. An ethanologen for inhibiting contaminant lactic acid bacteria present in a biofuel manufacturing process, comprising an ethanologen that is a lactic acid bacterium engineered to produce a biofuel and further engineered to produce a bacteriocin which inhibits contaminant lactic acid bacteria present in the biofuel manufacturing process;
   wherein the ethanologen comprises: (a) one or more endogenous genes encoding a mannitol dehydrogenase engineered to be inactive; (b) one or more exogenous genes encoding a pyruvate decarboxylase and one or more exogenous genes encoding an alcohol dehydrogenase II; and (c) one or more exogenous genes required for production of a bacteriocin;
   whereby the resulting engineered lactic acid bacterium produces more biofuel than a wild-type lactic acid bacterium having the same genetic background in a biofuel manufacturing process and reduces lactate and acetate production in said process by secretion of the bacteriocin, which inhibits contaminant lactic acid bacteria.

2. The ethanologen of claim 1, wherein the ethanologen is capable of fermenting sugars not naturally or not preferentially utilized by a main fermenting microbe present in the biofuel manufacturing process.

3. The ethanologen of claim 2, wherein the main fermenting microbe is *Saccharomyces cerevisiae*.

4. The ethanologen of claim 1, wherein the lactic acid bacterium is *Lactobacillus* sp., *Lactococcus* sp., *Enterococcus*, sp. or *Streptococcus* sp.

5. The ethanologen of claim 1, wherein the biofuel is ethanol or isobutanol.

6. The ethanologen of claim 1, wherein the bacteriocin is a Class I or Class II bacteriocin.

7. The ethanologen of claim 1, wherein the bacteriocin is pediocin, nisin, brochocin-C, or carnocyclin A.

8. The ethanologen of claim 1, wherein the ethanologen is *Lactobacillus* sp. engineered to produce the bacteriocin.

9. The ethanologen of claim 8, wherein the *Lactobacillus* sp. is *Lactobacillus casei*.

10. The ethanologen of claim 1, wherein the exogenous genes required for production of the bacteriocin are operably-linked to an inducible promoter.

11. The ethanologen of claim 1, further comprising one or more immunity genes conferring resistance to the ethanologen against said bacteriocin.

12. The ethanologen of claim 1, wherein the ethanologen is for producing ethanol from one or more carbohydrates and the carbohydrate is a lignocellulosic feedstock.

13. The ethanologen of claim 1, wherein the biofuel manufacturing process is an antibiotic-free process.

14. A method of making an ethanologen, comprising:
   (a) inactivating within a lactic acid bacterium one or more endogenous genes encoding a mannitol dehydrogenase;
   (b) introducing into a lactic acid bacterium one or more exogenous genes encoding a pyruvate decarboxylase and one or more exogenous genes encoding an alcohol dehydrogenase II; and
   (c) introducing into said lactic acid bacterium one or more exogenous genes required for production of a bacteriocin;
   whereby the resulting engineered bacterium produces more biofuel than a wild-type lactic acid bacterium having the same genetic background in a biofuel manufacturing process and reduces lactate and acetate production in said process by secretion of the bacteriocin, which inhibits contaminant lactic acid bacteria.

15. The method of claim 14, further comprising the steps of:
   (e) inactivating within the lactic acid bacterium genes encoding proteins associated with catabolite repression or elements related to catabolite repression;
   (f) removing DNA sequences encoding catabolite responsive elements (cre) that are involved in repressing the expression of genes required for uptake and metabolism of sugars not naturally or not preferentially utilized by *Saccharomyces cerevisiae* yeast;
   (g) introducing into the lactic acid bacterium one or more exogenous genes required for uptake and metabolism of sugars not naturally or not preferentially utilized by *Saccharomyces cerevisiae* yeast; and
   (h) introducing into the lactic acid bacterium one or more genes for hop- and/or antibiotic-resistance.

16. An ethanologen for use in an ethanol manufacturing process, comprising a *Lactobacillus casei* 12A derivative having:
   a deletion mutation ΔL-ldh1, an exogenous gene encoding a pyruvate decarboxylase, and an exogenous gene encoding an alcohol dehydrogenase II, wherein the exogenous genes are operably linked to a native *L. casei* promoter, wherein the engineered bacterium produces ethanol at a greater rate than a wild-type *Lactobacillus casei* 12A bacterium having the same genetic background, and
   wherein the ethanologen is capable of fermenting sugars not naturally or not preferentially utilized by a main fermenting microbe present in the ethanol manufacturing process
   wherein the ethanologen further comprises one or more mannitol dehydrogenases engineered to be inactive
   whereby the resulting engineered lactic acid bacterium produces more biofuel than a wild-type lactic acid bacterium having the same genetic background in a biofuel manufacturing process and reduces lactate and acetate production in said process by secretion of the bacteriocin, which inhibits contaminant lactic acid bacteria.

17. A method of inhibiting contaminant lactic acid bacteria in a biofuel manufacturing process, comprising:
   (a) culturing an ethanologen of claim 1 on a substrate comprising a carbohydrate;
   (b) inhibiting contaminant lactic acid bacteria present in the process by the ethanologen's secretion of a bacteriocin; and
   (c) collecting a biofuel produced by the process.

18. A method of reducing lactate and acetate production in a biofuel manufacturing process, comprising:
   (a) culturing an ethanologen of claim 1 on a substrate comprising a carbohydrate;
   (b) reducing lactate and acetate production by contaminant lactic acid bacteria present in the process by the ethanologen's secretion of a bacteriocin; and
   (c) collecting a biofuel produced by the process.

19. The ethanologen of claim 1, wherein the ethanologen further comprises the following: (a) genes encoding proteins associated with catabolite repression or elements related to catabolite repression engineered to be inactive; (b) DNA sequences encoding catabolite responsive elements (cre) that are involved in repressing the expression of genes required for uptake and metabolism of sugars not naturally or not preferentially utilized by *Saccharomyces cerevisiae* yeast engineered to be removed; (c) one or more exogenous genes required for uptake and metabolism of sugars not naturally or not preferentially utilized by *Saccharomyces cerevisiae* yeast; and (d) one or more genes for hop- and/or antibiotic-resistance.

* * * * *